US011104881B2

(12) United States Patent
Ying et al.

(10) Patent No.: US 11,104,881 B2
(45) Date of Patent: Aug. 31, 2021

(54) METHOD FOR HIGHLY EFFICIENT CONVERSION OF HUMAN STEM CELLS TO LINEAGE-SPECIFIC NEURONS

(71) Applicants: THE JOHNS HOPKINS UNIVERSITY, Baltimore, MD (US); KENNEDY KRIEGER INSTITUTE, INC., Baltimore, MD (US)

(72) Inventors: Mingyao Ying, Ellicott City, MD (US); John Laterra, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 366 days.

(21) Appl. No.: 15/954,983

(22) Filed: Apr. 17, 2018

(65) Prior Publication Data
US 2018/0305663 A1    Oct. 25, 2018

Related U.S. Application Data

(62) Division of application No. 15/100,682, filed as application No. PCT/US2014/068273 on Dec. 3, 2014, now abandoned.

(60) Provisional application No. 61/911,238, filed on Dec. 3, 2013.

(51) Int. Cl.
| | |
|---|---|
| *C12N 5/0793* | (2010.01) |
| *A61K 35/30* | (2015.01) |
| *C12N 15/85* | (2006.01) |
| *C12N 15/86* | (2006.01) |

(52) U.S. Cl.
CPC ........... *C12N 5/0619* (2013.01); *A61K 35/30* (2013.01); *C12N 15/85* (2013.01); *C12N 15/86* (2013.01); *C12N 2500/38* (2013.01); *C12N 2501/01* (2013.01); *C12N 2501/115* (2013.01); *C12N 2501/119* (2013.01); *C12N 2501/13* (2013.01); *C12N 2501/15* (2013.01); *C12N 2501/41* (2013.01); *C12N 2501/60* (2013.01); *C12N 2506/02* (2013.01); *C12N 2506/08* (2013.01); *C12N 2506/45* (2013.01); *C12N 2510/00* (2013.01); *C12N 2533/32* (2013.01); *C12N 2533/52* (2013.01); *C12N 2740/15043* (2013.01); *C12N 2799/027* (2013.01)

(58) Field of Classification Search
CPC .............. C12N 5/0619; C12N 2506/00; C12N 2506/02; C12N 2506/03; C12N 2506/45
See application file for complete search history.

(56) References Cited

U.S. PATENT DOCUMENTS

| | | |
|---|---|---|
| 2006/0134789 A1 | 6/2006 | Sugaya et al. |
| 2007/0231302 A1 | 10/2007 | Trapp et al. |
| 2012/0107284 A1 | 5/2012 | Kozlova |
| 2013/0108669 A1 | 5/2013 | Cooper et al. |
| 2013/0236436 A1* | 9/2013 | Zhang ................. C12N 5/0619 424/93.21 |

FOREIGN PATENT DOCUMENTS

WO    2011-050476 A1    5/2011

OTHER PUBLICATIONS

Martinat C, et al. "Cooperative transcription activation by Nurr1 and Pitx3 induces embryonic stem cell maturation to the midbrain dopamine neuron phenotype" Proc Natl Acad Sci USA. 2006;103:2874-2879.

Chung S, et al. "The homeodomain transcription factor Pitx3 facilitates differentiation of mouse embryonic stem cells into AHD2-expressing dopaminergic neurons" Mol Cell Neurosci. 2005;28:241-252.

Sanchez-Danes A, et al. "Efficient generation of A9 midbrain dopaminergic neurons by lentiviral delivery of LMX1A in human embryonic stem cells and induced pluripotent stem cells" Hum Gene Ther. 2012;23:56-69.

Lee HS, et al. "Foxa2 and Nurr1 synergistically yield A9 nigral dopamine neurons exhibiting improved differentiation, function, and cell survivaL" Stem Cells. 2010;28:501-512.

Flora A, et al. (2009). "Deletion of Atoh1 disrupts sonic hedgehog signaling in the developing cerebellum and prevents medulloblastoma" Science 326 (5958): 1424-1427.

Ayrault O, et al. (2010) "Atoh1 inhibits neuronal differentiation and collaborates with Gli1 to generate medulloblastoma-initiating cells". Cancer Research, 70, 5618.

Klisch TJ, et al. (2011). "In vivo Atoh1 targetome reveals how a proneural transcription factor regulates cerebellar development" PNAS vol. 108 No. 8 3288-3293.

Bermingham NA, et al. "Math1: an essential gene for the generation of inner ear hair cells" Science. 1999;284:1837-1841.

Ben-Aire N, Bellen HJ, Armstrong DL et al. Math1 is essential for genesis of cerebellar granule neurons. Nature. 1997;390:169-172.

(Continued)

*Primary Examiner* — Marcia S Noble

(74) *Attorney, Agent, or Firm* — Johns Hopkins Tech Ventures

(57) ABSTRACT

The present invention relates to the field of stem cells. More specifically, the present invention provides methods and compositions useful for the highly efficient conversion of human stem cells to lineage-specific neurons. In a specific embodiment, a method of inducing differentiation of human stem cells into dopaminergic (DA) neurons comprises the steps of (a) transfecting human stem cells with a lentiviral vector encoding Atoh1, wherein the vector is Dox inducible; and (b) growing the transfected cells in culture in the presence of Dox, Sonic Hedgehog (SHH) and FGF-8b until DA neurons are induced.

6 Claims, 20 Drawing Sheets

Specification includes a Sequence Listing.

(56) References Cited

OTHER PUBLICATIONS

Miesengaes GR, et al. "Identification and subclassification of new Atoh1 derived cell populations during mouse spinal cord development". Dev Biol. 2009;327:339-351.

Bertrand N, et al. Proneural genes and the specification of neural cell types. Nat Rev Neurosci. 2002;3:517-530.

Akazawa C, et al. A mammalian helix-loop-helix factor structurally related to the product of *Drosophila* proneural gene atonal is a positive transcriptional regulator expressed in the developing nervous system. J Biol Chem. 1995;270:8730-8738.

Kriks S, et al. "Dopamine neurons derived from human ES cells efficiently engraft in animal models of Parkinson's disease". Nature. 2011;480:547-551.

Grace AA, et al. The control of firing pattern in nigral dopamine neurons: burst firing. J Neurosci 1984;4:2877-2890.

Grace AA, et al. "The control of firing pattern in nigral dopamine neurons: single spike firing" J Neurosci. 1984;4:2866-2876.

Guzman J., et al. Robust pacemaking in substantia nigra dopaminergic neurons. J Neurosci 2009;29:11011-11019.

Warren L, et al. "Highly efficient reprogramming to pluripotency and directed differentiation of human cells with synthetic modified mRNA". Cell Stem Cell. 2010;7:618-630.

Kim D, et al. "Generation of human induced pluripotent stem cells by direct delivery of reprogramming proteins". Cell Stem Cell. 2009;4:472-476.

Sinha S, et al. "Purmorphamine activates the Hedgehog pathway by targeting Smoothened". Nat Chem Biol 2006;2:29-30.

Pournasr, B., (2011) "Concise review: alchemy of biology: generating desired cell types from abundant and accessible cells", Stem Cells, vol. 29, pp. 1933-1941.

Roybon, L., (2009) "Neurogenin2 directs granule neuroblast production and amplification while neuroD1 specifies neuronal fate during hippocampal neurogenesis", PLoS ONE, vol. 4, No. 3, e4779.

Sagal, J., (2014) "Proneural transcription factor atoh1 drives highly efficient differentiation of human pluripotent stem cells into dopaminergic neurons", Stem Cells Translational Medicine, vol. 3, pp. 888-898.

Srivastava, R., (2013) "Conditional induction of math1 specifies embryonic stem cells to cerebellar granule neuron lineage and promotes differentiation into mature granule neurons", Stem Cells, vol. 31, pp. 652-665.

\* cited by examiner

A

B

C

SEQUENCE LISTING

```
<160> NUMBER OF SEQ ID NOS: 9

<210> SEQ ID NO 1
<211> LENGTH: 1065
<212> TYPE: DNA
<213> ORGANISM: Homo sapiens
<220> FEATURE:
<221> NAME/KEY: misc_feature
<222> LOCATION: (1)..(1065)
<223> OTHER INFORMATION: Human Atoh1 nucleic acid sequence

<400> SEQUENCE: 1
atgtcccgcc tgctgcatgc agaagagtgg gctgaagtga aggagttggg agaccaccat      60
cgccagcccc agccgcatca tctcccgcaa ccgccgccgc cgccgcagcc acctgcaact     120
ttgcaggcga gagagcatcc cgtctacccg cctgagctgt ccctcctgga cagcaccgac     180
ccacgcgcct ggctggctcc cactttgcag ggcatctgca cggcacgcgc cgcccagtat     240
ttgctacatt ccccggagct gggtgcctca gaggccgctg cgccccggga cgaggtggac     300
ggccgggggg agctggtaag gaggagcagc ggcggtgcca gcagcagcaa gagccccggg     360
ccggtgaaag tgcgggaaca gctgtgcaag ctgaaaggcg gggtggtggt agacgagctg     420
ggctgcagcc gccaacgggc cccttccagc aaacaggtga atggggtgca gaagcagaga     480
cggctagcag ccaacgccag ggagcggcgc aggatgcatg ggctgaacca cgccttcgac     540
cagctgcgca atgttatccc gtcgttcaac aacgacaaga agctgtccaa atatgagacc     600
ctgcagatgg cccaaatcta catcaacgcc ttgtccgagc tgctacaaac gcccagcgga     660
ggggaacagc caccgccgcc tccagcctcc tgcaaaagcg accaccacca ccttcgcacc     720
gcggcctcct atgaaggggg cgcgggcaac gcgaccgcag ctgggctca gcaggcttcc     780 ggagggagcc agcggccgac cccgcccggg agttgccgga ctcgcttctc agccccagct     840
tctgcgggag ggtactcggt gcagctggac gctctgcact tctcgacttt cgaggacagc     900
gccctgacag cgatgatggc gcaaaagaat ttgtctcctt ctctccccgg gagcatcttg     960
cagccagtgc aggaggaaaa cagcaaaact tcgcctcggt cccacagaag cgacgggaa    1020 ttttcccccc attcccatta cagtgactcg gatgaggcaa gttag                    1065

<210> SEQ ID NO 2
<211> LENGTH: 354
<212> TYPE: PRT
<213> ORGANISM: Homo sapiens
<220> FEATURE:
<221> NAME/KEY: MISC_FEATURE
<222> LOCATION: (1)..(354)
```

<223> OTHER INFORMATION: Human Atoh1 amino acid sequence

<400> SEQUENCE: 2

```
Met Ser Arg Leu Leu His Ala Glu Glu Trp Ala Glu Val Lys Glu Leu
1               5                   10                  15

Gly Asp His His Arg Gln Pro Gln Pro His His Leu Pro Gln Pro Pro
                20                  25                  30

Pro Pro Pro Gln Pro Pro Ala Thr Leu Gln Ala Arg Glu His Pro Val
            35                  40                  45

Tyr Pro Pro Glu Leu Ser Leu Leu Asp Ser Thr Asp Pro Arg Ala Trp
50                  55                  60

Leu Ala Pro Thr Leu Gln Gly Ile Cys Thr Ala Arg Ala Ala Gln Tyr
65                  70                  75                  80

Leu Leu His Ser Pro Glu Leu Gly Ala Ser Glu Ala Ala Ala Pro Arg
                85                  90                  95

Asp Glu Val Asp Gly Arg Gly Glu Leu Val Arg Arg Ser Ser Gly Gly
                100                 105                 110

Ala Ser Ser Ser Lys Ser Pro Gly Pro Val Lys Val Arg Glu Gln Leu
            115                 120                 125

Cys Lys Leu Lys Gly Gly Val Val Val Asp Glu Leu Gly Cys Ser Arg
130                 135                 140

Gln Arg Ala Pro Ser Ser Lys Gln Val Asn Gly Val Gln Lys Gln Arg
145                 150                 155                 160

Arg Leu Ala Ala Asn Ala Arg Glu Arg Arg Arg Met His Gly Leu Asn
                165                 170                 175

His Ala Phe Asp Gln Leu Arg Asn Val Ile Pro Ser Phe Asn Asn Asp
                180                 185                 190

Lys Lys Leu Ser Lys Tyr Glu Thr Leu Gln Met Ala Gln Ile Tyr Ile
            195                 200                 205

Asn Ala Leu Ser Glu Leu Leu Gln Thr Pro Ser Gly Gly Glu Gln Pro
210                 215                 220

Pro Pro Pro Pro Ala Ser Cys Lys Ser Asp His His His Leu Arg Thr
225                 230                 235                 240

Ala Ala Ser Tyr Glu Gly Gly Ala Gly Asn Ala Thr Ala Ala Gly Ala
                245                 250                 255

Gln Gln Ala Ser Gly Gly Ser Gln Arg Pro Thr Pro Pro Gly Ser Cys
                260                 265                 270

Arg Thr Arg Phe Ser Ala Pro Ala Ser Ala Gly Gly Tyr Ser Val Gln
            275                 280                 285

Leu Asp Ala Leu His Phe Ser Thr Phe Glu Asp Ser Ala Leu Thr Ala
290                 295                 300

Met Met Ala Gln Lys Asn Leu Ser Pro Ser Leu Pro Gly Ser Ile Leu
305                 310                 315                 320

Gln Pro Val Gln Glu Glu Asn Ser Lys Thr Ser Pro Arg Ser His Arg
                325                 330                 335

Ser Asp Gly Glu Phe Ser Pro His Ser His Tyr Ser Asp Ser Asp Glu
                340                 345                 350

Ala Ser
```

<210> SEQ ID NO 3
<211> LENGTH: 1134
<212> TYPE: DNA
<213> ORGANISM: Homo sapiens
<220> FEATURE:
<221> NAME/KEY: misc_feature
<222> LOCATION: (1)..(1134)
<223> OTHER INFORMATION: Human Atoh1 nucleic acid sequence with N-
       terminal flag tag

<400> SEQUENCE: 3

```
atggactaca aagaccatga cggtgattat aaagatcatg atatcgatta caaggatgac    60
gatgacaaga tgtcccgcct gctgcatgca gaagagtggg ctgaagtgaa ggagttggga   120
gaccaccatc gccagcccca gccgcatcat ctcccgcaac cgccgccgcc gcgcagcca   180
cctgcaactt tgcaggcgag agagcatccc gtctacccgc ctgagctgtc cctcctggac   240
agcaccgacc cacgcgcctg gctggctccc actttgcagg gcatctgcac ggcacgcgcc   300
gcccagtatt tgctacattc cccggagctg gtgcctcag aggccgctgc gccccgggac   360
gaggtggacg gccggggga gctggtaagg aggagcagcg gcggtgccag cagcagcaag   420
agccccgggc cggtgaaagt gcgggaacag ctgtgcaagc tgaaaggcgg ggtggtggta   480
gacgagctgg gctgcagccg ccaacgggcc ccttccagca acaggtgaa tggggtgcag   540
aagcagagac ggctagcagc caacgccagg gagcggcgca ggatgcatgg gctgaaccac   600
gccttcgacc agctgcgcaa tgttatcccg tcgttcaaca acgacaagaa gctgtccaaa   660
tatgagaccc tgcagatggc ccaaatctac atcaacgcct gtccgagct gctacaaacg   720
cccagcggag gggaacagcc accgccgcct ccagcctcct gcaaaagcga ccaccaccac   780
cttcgcaccg cggcctccta tgaaggggc gcgggcaacg cgaccgcagc tggggctcag   840
caggcttccg gagggagcca gcggccgacc ccgcccggga gttgccggac tcgcttctca   900
gccccagctt ctgcgggagg gtactcggtg cagctggacg tctgcacttt ctcgactttc   960
gaggacagcg ccctgacagc gatgatggcg caaaagaatt tgtctccttc tctccccggg  1020
agcatcttgc agccagtgca ggaggaaaac agcaaaactt cgcctcggtc ccacagaagc  1080
gacgggaat tttcccccca ttcccattac agtgactcgg atgaggcaag ttag        1134
```

<210> SEQ ID NO 4
<211> LENGTH: 377
<212> TYPE: PRT
<213> ORGANISM: Homo sapiens
<220> FEATURE:
<221> NAME/KEY: MISC_FEATURE
<222> LOCATION: (1)..(377)
<223> OTHER INFORMATION: Human Atoh1 amino acid sequence with N-terminal
       flag tag

<400> SEQUENCE: 4

```
Met Asp Tyr Lys Asp His Asp Gly Asp Tyr Lys Asp His Asp Ile Asp
1               5                   10                  15

Tyr Lys Asp Asp Asp Asp Lys Met Ser Arg Leu Leu His Ala Glu Glu
            20                  25                  30

Trp Ala Glu Val Lys Glu Leu Gly Asp His His Arg Gln Pro Gln Pro
        35                  40                  45

His His Leu Pro Gln Pro Pro Pro Pro Gln Pro Pro Ala Thr Leu
    50                  55                  60

Gln Ala Arg Glu His Pro Val Tyr Pro Pro Glu Leu Ser Leu Leu Asp
65                  70                  75                  80

Ser Thr Asp Pro Arg Ala Trp Leu Ala Pro Thr Leu Gln Gly Ile Cys
                85                  90                  95

Thr Ala Arg Ala Ala Gln Tyr Leu Leu His Ser Pro Glu Leu Gly Ala
            100                 105                 110

Ser Glu Ala Ala Ala Pro Arg Asp Glu Val Asp Gly Arg Gly Glu Leu
```

```
            115                 120                 125
Val Arg Arg Ser Ser Gly Gly Ala Ser Ser Lys Ser Pro Gly Pro
    130                 135                 140

Val Lys Val Arg Glu Gln Leu Cys Lys Leu Lys Gly Val Val
145                 150                 155                 160

Asp Glu Leu Gly Cys Ser Arg Gln Arg Ala Pro Ser Ser Lys Gln Val
                165                 170                 175

Asn Gly Val Gln Lys Gln Arg Arg Leu Ala Ala Asn Ala Arg Glu Arg
                180                 185                 190

Arg Arg Met His Gly Leu Asn His Ala Phe Asp Gln Leu Arg Asn Val
            195                 200                 205

Ile Pro Ser Phe Asn Asn Asp Lys Lys Leu Ser Lys Tyr Glu Thr Leu
    210                 215                 220

Gln Met Ala Gln Ile Tyr Ile Asn Ala Leu Ser Glu Leu Leu Gln Thr
225                 230                 235                 240

Pro Ser Gly Gly Glu Gln Pro Pro Pro Pro Ala Ser Cys Lys Ser
                245                 250                 255

Asp His His His Leu Arg Thr Ala Ala Ser Tyr Glu Gly Gly Ala Gly
                260                 265                 270

Asn Ala Thr Ala Ala Gly Ala Gln Gln Ala Ser Gly Gly Ser Gln Arg
            275                 280                 285

Pro Thr Pro Pro Gly Ser Cys Arg Thr Arg Phe Ser Ala Pro Ala Ser
    290                 295                 300

Ala Gly Gly Tyr Ser Val Gln Leu Asp Ala Leu His Phe Ser Thr Phe
305                 310                 315                 320

Glu Asp Ser Ala Leu Thr Ala Met Met Ala Gln Lys Asn Leu Ser Pro
                325                 330                 335

Ser Leu Pro Gly Ser Ile Leu Gln Pro Val Gln Glu Glu Asn Ser Lys
                340                 345                 350

Thr Ser Pro Arg Ser His Arg Ser Asp Gly Glu Phe Ser Pro His Ser
            355                 360                 365

His Tyr Ser Asp Ser Asp Glu Ala Ser
    370                 375

<210> SEQ ID NO 5
<211> LENGTH: 819
<212> TYPE: DNA
<213> ORGANISM: Homo sapiens
<220> FEATURE:
<221> NAME/KEY: misc_feature
<222> LOCATION: (1)..(819)
<223> OTHER INFORMATION: Human Neurogenin2 nucleic acid sequence

<400> SEQUENCE: 5
atgttcgtca atccgagac cttggagttg aaggaggaag aggacgtgtt agtgctgctc      60
ggatcggcct cccccgcctt ggcggccctg accccgctgt catccagcgc cgacgaagaa     120
gaggaggagg agccgggcgc gtcaggcggg gcgcgtcggc agcgcgggc tgaggccggg     180 caggggcgc ggggcggcgt ggctgcgggt gcggagggct gccggcccgc acggctgctg     240
ggtctggtac acgattgcaa acggcgccct tccggggcgc gggccgtctc ccgaggcgcc     300
aagacggccg agacggtgca gcgcatcaag aagacccgta gactgaaggc caacaaccgc     360
gagcgaaacc gcatgcacaa cctcaacgcg gcactggacg cgctgcgcga ggtgctcccc     420
acgttccccg aggacgccaa gctcaccaag atcgagaccc tgcgcttcgc ccacaactac     480
atctgggcac tcaccgagac cctgcgcctg gcggatcact gcggggcgg cggcggggc     540
```

-continued

```
ctgccggggg cgctcttctc cgaggcagtg ttgctgagcc cgggaggagc cagcgccgcc    600
ctgagcagca gcggagacag ccoctcgccc gcctccacgt ggagttgcac caacagcccc    660
gcgccgtcct cctccgtgtc ctccaattcc acctcccct acagctgcac tttatcgccc     720
gccagcccgg ccgggtcaga catggactat tggcagcccc cacctcccga caagcaccgc    780
tatgcacctc acctccccat agccagggat tgtatctag                           819
```

```
<210> SEQ ID NO 6
<211> LENGTH: 272
<212> TYPE: PRT
<213> ORGANISM: Homo sapiens
<220> FEATURE:
<221> NAME/KEY: MISC_FEATURE
<222> LOCATION: (1)..(272)
<223> OTHER INFORMATION: Human Neurogenin2 amino acid sequence

<400> SEQUENCE: 6
```

```
Met Phe Val Lys Ser Glu Thr Leu Glu Leu Lys Glu Glu Asp Val
1               5                   10                  15

Leu Val Leu Leu Gly Ser Ala Ser Pro Ala Leu Ala Ala Leu Thr Pro
                20                  25                  30

Leu Ser Ser Ser Ala Asp Glu Glu Glu Glu Glu Pro Gly Ala Ser
        35                  40                  45

Gly Gly Ala Arg Arg Gln Arg Gly Ala Glu Ala Gly Gln Gly Ala Arg
50                  55                  60

Gly Gly Val Ala Ala Gly Ala Glu Gly Cys Arg Pro Ala Arg Leu Leu
65                  70                  75                  80

Gly Leu Val His Asp Cys Lys Arg Arg Pro Ser Arg Ala Arg Ala Val
                85                  90                  95

Ser Arg Gly Ala Lys Thr Ala Glu Thr Val Gln Arg Ile Lys Lys Thr
            100                 105                 110

Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Gly Gly
                165                 170                 175

Gly Gly Gly Gly Leu Pro Gly Ala Leu Phe Ser Glu Ala Val Leu Leu
            180                 185                 190

Ser Pro Gly Gly Ala Ser Ala Ala Leu Ser Ser Ser Gly Asp Ser Pro
        195                 200                 205

Ser Pro Ala Ser Thr Trp Ser Cys Thr Asn Ser Pro Ala Pro Ser Ser
    210                 215                 220

Ser Val Ser Ser Asn Ser Thr Ser Pro Tyr Ser Cys Thr Leu Ser Pro
225                 230                 235                 240

Ala Ser Pro Ala Gly Ser Asp Met Asp Tyr Trp Gln Pro Pro Pro Pro
                245                 250                 255

Asp Lys His Arg Tyr Ala Pro His Leu Pro Ile Ala Arg Asp Cys Ile
            260                 265                 270
```

```
<210> SEQ ID NO 7
<211> LENGTH: 1071
<212> TYPE: DNA
<213> ORGANISM: Homo sapiens
```

```
<220> FEATURE:
<221> NAME/KEY: misc_feature
<222> LOCATION: (1)..(1071)
<223> OTHER INFORMATION: Human NeuroD1 nucleic acid sequence

<400> SEQUENCE: 7
atgaccaaat cgtacagcga gagtgggctg atgggcgagc ctcagcccca aggtcctcca      60
agctggacag acgagtgtct cagttctcag gacgaggagc acgaggcaga caagaaggag     120
gacgacctcg aagccatgaa cgcagaggag gactcactga ggaacggggg agaggaggag     180
gacgaagatg aggacctgga agaggaggaa gaagaggaag aggaggatga cgatcaaaag     240
cccaagagac gcggccccaa aaagaagaag atgactaagg ctcgcctgga gcgttttaaa     300
ttgagacgca tgaaggctaa cgcccgggag cggaaccgca tgcacggact gaacgcggcg     360
ctagacaacc tgcgcaaggt ggtgcccttg cattctaaga cgcagaagct gtccaaaatc     420
gagactctgc gcttggccaa gaactacatc tgggctctgt cggagatcct gcgctcaggc     480
aaaagcccag acctggtctc cttcgttcag acgctttgca agggcttatc ccaacccacc     540
accaacctgg ttgcgggctg cctgcaactc aatcctcgga cttttctgcc tgagcagaac     600
caggacatgc cccccacct gccgacggcc agcgcttcct tccctgtaca cccctactcc     660
taccagtcgc ctgggctgcc cagtccgcct acggtacca tggacagctc ccatgtcttc     720
cacgttaagc tccgccgca cgcctacagc gcagcgctgg agcccttctt tgaaagccct     780
ctgactgatt gcaccagccc ttcctttgat ggacccctca gcccgccgct cagcatcaat     840
ggcaacttct ctttcaaaca cgaaccgtcc gccgagtttg agaaaaatta tgcctttacc     900
atgcactatc ctgcagcgac actggcaggg gcccaaagcc acggatcaat cttctcaggc     960
accgctgccc ctcgctgcga gatccccata gacaatatta tgtccttcga tagccattca    1020
catcatgagc gagtcatgag tgcccagctc aatgccatat ttcatgatta g             1071

<210> SEQ ID NO 8
<211> LENGTH: 356
<212> TYPE: PRT
<213> ORGANISM: Homo sapiens
<220> FEATURE:
<221> NAME/KEY: MISC_FEATURE
<222> LOCATION: (1)..(356)
<223> OTHER INFORMATION: Human NeuroD1 amino acid sequence

<400> SEQUENCE: 8

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125
```

```
Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
275                 280                 285

Pro Ser Ala Glu Phe Glu Lys Asn Tyr Ala Phe Thr Met His Tyr Pro
        290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
            355

<210> SEQ ID NO 9
<211> LENGTH: 356
<212> TYPE: PRT
<213> ORGANISM: Homo sapiens
<220> FEATURE:
<221> NAME/KEY: MISC_FEATURE
<222> LOCATION: (1)..(356)
<223> OTHER INFORMATION: Human NeuroD1 amino acid sequence alt.

<400> SEQUENCE: 9

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Thr Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Asp Asp Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
```

```
                    115                 120                 125
Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355
```

METHOD FOR HIGHLY EFFICIENT CONVERSION OF HUMAN STEM CELLS TO LINEAGE-SPECIFIC NEURONS

CROSS-REFERENCE TO RELATED APPLICATIONS

This application is a Divisional of U.S. patent application Ser. No. 15/100,682, filed Jun. 1, 2016, which is a 35 U.S.C. § 371 U.S. national entry of International Application PCT/US2014/068273, having an international filing date of Dec. 3, 2014, which claims the benefit of U.S. Provisional Application No. 61/911,238, filed Dec. 3, 2013, the content of each of the aforementioned applications is herein incorporated in their entirety.

FIELD OF THE INVENTION

The present invention relates to the field of stem cells. More specifically, the present invention provides methods and compositions useful for the highly efficient conversion of human stem cells to lineage-specific neurons.

INCORPORATION-BY-REFERENCE OF MATERIAL SUBMITTED ELECTRONICALLY

This application contains a sequence listing. It has been submitted electronically via EFS-Web as an ASCII text file entitled "P12596-02_ST25.txt." The sequence listing is 21,808 bytes in size, and was created on Dec. 3, 2014. It is hereby incorporated by reference in its entirety.

BACKGROUND OF THE INVENTION

Optimized differentiation strategies are essential for differentiating human stem cells (SCs) into lineage-specific neuronal progenies in sufficient numbers and purity for transplantation or disease modeling. Current strategies for generating lineage-specific neurons from human pluripotent or multipotent stem cells, including induced pluripotent cells (iPSCs), embryonic stem cells (ESCs) and fetal neural stem cells (NSCs), generally yields incomplete neuronal conversion and lineage specification, which adversely affects in vivo engraftment and function of these neurons and also leads to considerable safety concerns regarding their potential for malignancy formation or neural overgrowth. The present invention provides a novel and optimized strategy for highly efficient differentiation of human SCs to lineage-specific and functional neurons.

SUMMARY OF THE INVENTION

The present invention is based, at least in part, on the development of methods for using transcription factors including Atoh1, Neurogenin 2, and NeuroD1, to drive highly efficient neuronal differentiation of human SCs into lineage-specific neurons, such as dopaminergic (DA) neurons.

Cell replacement therapy using human stem cells (SCs) holds great promise for treating neurological diseases in which neuronal loss results in cognitive, extrapyramidal, and/or motor dysfunction. Optimized differentiation strategies are essential to differentiate human stem cells into lineage-specific neuronal progenies in sufficient numbers and purity for transplantation or disease modeling. As described herein, we have established a strategy for differentiating human pluripotent or multipotent SCs into lineage-specific and functional neurons. We found a defined transcription factor that can induce the highly efficient conversion of human SCs to lineage-specific neurons (e.g., dopaminergic (DA) neurons). This strategy can generate dopaminergic neurons with >80% purity. The established strategy is novel and highly applicable for disease modeling and cell replacement therapy for several neurological disorders, including but not limited to Parkinson's disease, spinal cord injury, amyotrophic lateral sclerosis and hearing loss.

Current differentiation strategies for converting human SCs to neurons act primarily on cell surface receptors or intracellular signaling proteins to alter the level of multiple downstream transcription factors and in turn to change the gene expression profile and cell fate specification. These strategies lack specificity and efficiency because they activate multiple signaling cascades and transcription factors, only a fraction of which are optimal and necessary to drive lineage-specific neuronal differentiation. In certain embodiments, our differentiation strategy uses a single transcription factor Atoh1 to induce highly specific neuronal differentiation signaling, resulting in rapid and highly efficient lineage-specific neuronal conversion. In other embodiments, the strategy may include NeuroD1 and/or Neurogenin 2. Our differentiation strategy saves the time for generating lineage-specific neurons from human SCs by at least 50%. It also generates lineage-specific neurons with >80% purity, significantly higher than the purity (10-40%) normally achieved by other methods.

Accordingly, in one aspect, the present invention provides methods for differentiating stem cells into neuronal cells. In one embodiment, a method for inducing differentiation of neuronal cells from human stem cells comprises the steps of (a) transfecting human stem cells with an expression vector encoding Atoh1; and (b) growing the transfected cells in culture until the stem cells are differentiated. In certain embodiments, the human stem cells are induced pluripotent stem cells (iPSCs), embryonic stem cells (ESCs) or neural stem cells (NSCs). In specific embodiments, the neural stem cells are fetal or adult neural stem cells.

In particular embodiments, Atoh1 comprises SEQ ID NO:2. In other embodiments, Atoh1 comprises an N-terminal flag tag and is shown, for example, in SEQ ID NO:4.

In other embodiments, the expression vector is a viral vector. In particular embodiments, the viral vector is from a lentivirus, adeno-associated virus, herpes simplex virus, Senai virus or baculovirus. In a specific embodiment, the viral vector is from a lentivirus. In other embodiments, the expression vector is non-viral. In a further embodiment, the expression vector encoding Atoh1 is inducible. In a specific embodiment, the lentiviral expression vector is doxycycline (Dox) inducible.

In a further embodiment, the cells are grown in the presence of a sufficient concentration of Doxycycline (Dox) in order to induce Atoh1 transgene expression and drive the differentiation of human stem cells into neuronal cells. In a more specific embodiment, step (b) further comprises the steps outlined in Table 1. In yet another embodiment, prior to step (b), the method further comprises the step of transfecting the human stem cells with an expression vector encoding NeuroD1. In a particular embodiment, NeuroD1 comprises SEQ ID NO:8. In an alternative embodiment, NeuroD1 comprises SEQ ID NO:9. In another embodiment, prior to step (b), the method further comprises the step of transfecting the human stem cells with an expression vector encoding Neurogenin 2. In a particular embodiment, Neurogenin 2 comprises SEQ ID NO:6. In alternative embodiments, the expression vector of step (a) also encodes Neurogenin 2 and/or NeuroD1. The present invention further contemplates the use of biologically active or functional fragments of Atoh1, Neurogenin 2 and/or NeuroD1 in the present invention. Furthermore, the methods of the present invention can further comprise exposing the cells to sufficient concentrations of additional growth factors.

In a specific embodiment, a method of inducing differentiation of human stem cells into dopaminergic (DA) neurons comprises the steps of (a) transfecting human stem cells with a lentiviral vector encoding Atoh1, wherein the vector is Dox inducible; and (b) growing the transfected cells in culture in the presence of Dox, Sonic Hedgehog (SHH) and FGF-8b until DA neurons are induced. In one embodiment, the human stem cells are iPSCs. In another embodiment, the human stem cells are ESCs. In such embodiments, step (b) further comprises the steps outlined in Table 2. In an alternative embodiment, the human stem cells are NSCs. In such embodiment, step (b) further comprises the steps outlined in Table 3. In yet another embodiment, prior to step (b), the method further comprises the step of transfecting the human stem cells with an expression vector encoding NeuroD1. In another embodiment, prior to step (b), the method further comprises the step of transfecting the human stem cells with an expression vector encoding Neurogenin 2. In alternative embodiments, the lentiviral vector of step (a) also encodes NeuroD1 and/or Neurogenin 2.

In another aspect, the present invention provides methods for treating patients suffering from a neurodegenerative disease. In one embodiment, a method for treating a patient suffering from a neurodegenerative disease comprises the steps of (a) obtaining stem cells from the patient; (b) initiating differentiation of the stem cells into a population of differentiated cells using a method described herein; (c) analyzing the development of differentiated neurons in culture; and (d) transplanting the differentiated cells into the patient's brain. In certain embodiments, the neurodegenerative disease is Parkinson's disease and the differentiated cells are DA neurons.

The present invention also provides a population of neuronal cells prepared using any one of the methods described herein.

DETAILED DESCRIPTION OF THE INVENTION

Figure 1A:
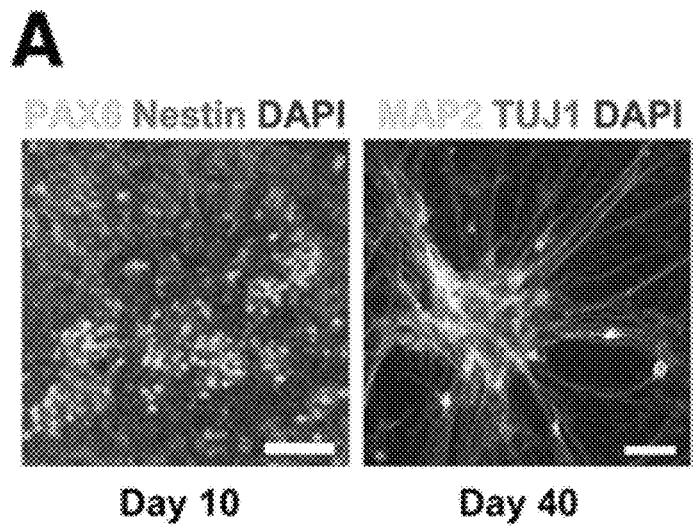
FIG. 1A-1C. Atoh1 is induced during the differentiation of human pluripotent stem cells into neurons. (A): Human induced pluripotent stem cells (iPSCs) were differentiated into neurons following the dual-SMAD inhibition protocol. By day 10 of differentiation, cells expressed neural lineage markers (PAX6 and NESTIN). By day 40 of differentiation, iPSC-derived neurons expressed neuronal markers (TUJ1 and MAP2). Cell nuclei were counterstained with DAPI. Scale bars=50 (B, C): Markers for pluripotent cells (NANOG), neural (PAX6), and neuronal (Ngn2 and NEUROD1) lineages were analyzed by quantitative real-time polymerase chain reaction (qRT-PCR) during iPSC differentiation at days 0, 10, and 20. Atoh1 expression was analyzed by qRT-PCR (B) and Western blotting (C). The data represent means±SEM. *, p<0.01 compared with day 0. Abbreviation: DAPI, 4',6-diamidino-2-phenylindole.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Human pluripotent stem cells (PSCs), including embryonic stem cells (ESCs) and induced pluripotent stem cells (iPSCs), exhibit unique characteristics such as indefinite self-renewal capacity and multi-lineage differentiation potential. Human PSCs, especially patient-derived iPSCs, hold enormous promise for various applications in regenerative medicine, including disease modeling, drug development and cell replacement therapy. In order to fully utilize these patient-specific iPSCs in regenerative medicine, highly efficient differentiation strategies are required to drive iPSCs into desired lineages and generate functional cell progenies, such as various subtypes of neurons. Current protocols for differentiating human PSCs into lineage-specific neurons (e.g., dopaminergic (DA) neurons) are based on embryoid body formation, stromal feeder co-culture, selective survival conditions or inhibitors of SMAD signaling. These PSC-derived neurons have allowed scientists to study molecular mechanisms underlying various neurological disorders, test potential drugs and optimize strategies for cell replacement therapy. However, current neuron differentiation protocols for PSCs involve months of stem cell culture procedures and multiple reagents, which cause significant variation especially for researchers who have limited practice in PSC culture and desire functional neurons at high purity for disease-in-a-dish models. A broad desire for a robust system to generate human PSC-derived neurons motivated us to develop a highly efficient strategy to generate lineage-specific functional neurons using the proneural transcription factor Atoh1.

ATOH1 (the mammalian homolog of *Drosophila Atonal*) belongs to the proneural transcription factors of the basic helix-loop-helix (bHLH) family. Proneural transcription factors are crucial in driving the acquisition of a generic neuronal fate and regulating neuronal subtype specification during development. Atoh1 proteins form heterodimers with E proteins, and these heterodimers function as transcriptional activators by binding E box motifs (CANNTG) in the regulatory regions of their target genes. Atoh1 is a key regulator of neurogenesis, governing the differentiation of various neuronal lineages, including cerebellar granule neurons, brainstem neurons, inner ear hair cells, and numerous components of the proprioceptive and interoceptive systems, as well as some nonneuronal cell types. Atoh1 can activate crucial neurogenic transcription factors, such as NeuroD1, 2, 6 and Nhlh1, 2, to initiate a neuronal differentiation program that later becomes self-supporting and Atoh1-independent. Certain members of the proneural transcription factor family, such as ASCL1, Ngn2 and NeuroD1, have been successfully used to generate neurons from both PSCs and somatic cells. However, the role of Atoh1 in the neuronal differentiation and neuron subtype specification of human PSCs is largely unknown, and, as a result, Atoh1-based strategies for the neuronal conversion of human PSCs is still unavailable.

Here, we show that Atoh1 is induced during the neuronal differentiation of human PSCs. By transiently inducing ectopic Atoh1 expression, we are able to efficiently convert PSCs into neurons. Atoh1 induction, in combination with two neural patterning morphogens (Sonic Hedgehog (SHH) and fibroblast growth factor 8b (FGF8b)), leads to rapid and highly efficient conversion of PSCs into DA neurons that recapitulate key biochemical and electrophysiological features of primary midbrain DA neurons. We also demonstrate that Atoh1-induced DA neurons serve as a reliable model for analyzing 6-OHDA-induced neurotoxicity in human midbrain DA neurons. Since most symptoms of Parkinson's disease (PD) result from the degeneration of midbrain DA neurons located in the substantia nigra, Atoh1-induced DA neurons provide an in vitro neuron model for mechanistic studies and drug testing for PD.

Here, we established a method for using Atoh1 to drive highly efficient neuronal differentiation of human SCs into lineage-specific neurons, such as DA neurons. Neuronal differentiation strategies are widely applicable to various kinds of human stem cells, including human embryonic stem cells, induced pluripotent cells, fetal/adult neural stem cells and mesenchymal stem cells. Thus, the present invention can be used in driving the neuronal differentiation of these stem cells.

Here, we used lentivirus to deliver Atoh1 gene into human stem cells. Atoh1 gene can also be delivered by other virus vectors, including but not limited to adeno-associated virus, herpes simplex virus, Sendai virus and baculovirus. Non-viral Atoh1 delivery is also feasible by using plasmid transfection, mRNA transfection and recombinant cell-penetrating protein. Certain chemical compounds can also be used to activate expression of endogenous Atoh1. See U.S. Patent Publication No. 20090232780.

Here, we used Atoh1 in the differentiation of human stem cells into dopaminergic neurons. Atoh1 is a key regulator of neurogenesis, governing the differentiation of various neuronal lineages (cerebellar granule and brainstem neurons, inner ear hair cells, and numerous components of the proprioceptive and interoceptive systems), as well as some nonneuronal cell types. We anticipate that Atoh1 can be used to differentiate human stem cells into different neuronal lineages, including but not limited to motor neurons, cerebellar neurons, inner ear hair cells, and numerous neuron lineages of the proprioceptive and interoceptive systems.

Here we used Atoh1 in combination with sonic hedgehog and FGF-8b as the morphogens to drive the differentiation of human SCs into DA neurons. Other reagents, such as puromorphamine and CHIR99021, have also been successfully used to drive the DA neuron differentiation of human SCs. Expression of specific genes, including but not limited to FOXA2, LMX1A, PITX3 and NURR1, has also been shown to differentiate human or mouse SCs into DA neurons. We anticipate that these reagents and genes can be incorporated into Atoh1-induced DA neuron differentiation protocol.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Proneural Transcription Factor Atoh1 Drives Highly Efficient Differentiation of Human Pluripotent Stems Cells into Dopaminergic Neurons Materials and Methods Cell Culture.

Human H1 ESC line was obtained from WiCell Research Resources (WiCell, WI). Human iPSC line ND27760 (passage 25-30) was derived from human skin fibroblasts from a PD patient with a SNCA triplication that were obtained from the Coriell Cell Repositories. Cell reprogramming was performed using non-integrating 4 factor (SOX2/OCT4/KLF4/MYC) Sendai virus system (CytoTune-iPS Reprogramming Kit, Life Technologies). The pluripotency of this iPSC line has been characterized by immunocytochemistry for pluripotent cell markers (NANOG, OCT4, TRA-1-60 and SSEA-3) and embryoid body differentiation. Human ESCs and iPSCs were maintained as feeder-free cultures in Essential 8 medium (Life Technologies) or mTESR1 medium (Stemcell Technologies) in 5% $CO_2$/95% air condition at 37° C., and were passaged using dispase (Life Technologies). Karyotype analysis of G-banded metaphase chromosomes was performed to confirm the chromosomal integrity of these ESCs and iPSCs. All experiments involving human stem cells were performed with the approval of the Johns Hopkins Medicine Institutional Review Boards.

Lentiviral Transduction.

Human Atoh1 cDNA was constructed using high-fidelity PCR kit (Roche) and cloned into pTRIPZ vector (Thermo Scientific) with AgeI and MluI. The nucleic acid and amino acid sequences for Atoh1 are shown in SEQ ID NOS:1-2, respectively. Trans-Lentiviral Packaging System (Thermo Scientific) was used for lentivirus packaging. Cells were infected by lentivirus at an MOI of 5 for 24 h with the addition of TransDux Virus Infection solution (System Biosciences). Stable cell lines were established by puromycin selection (0.5 μg/ml). All recombinant DNA and lentivirus experiments were performed following the National Institutes of Health guidelines.

Cell Differentiation and Cryopreservation.

To measure Atoh1 expression during the neuronal conversion of human PSCs, cells were differentiated following a dual-SMAD inhibition protocol (Chambers et al., 27 NAT. BIOTECHNOL. 275-80 (2009). Noggin in this protocol was replaced by LDN193189 (100 nM, Stemgent). For the Atoh1-induced neuron differentiation protocol, cells were plated ($8 \times 10^4$ cells per $cm^2$) on matrigel (BD) in Essential 8 Medium (Life Technologies) with the ROCK inhibitor (Y-27632, 10 μM, Stemgent). Atoh1 was induced by Doxycycline (0.5 μg/ml, Sigma-Aldrich) in culture medium from Day 1 to 5. From Day 1 to 3, cell culture medium was changed every day and gradually shifted from Essential 6 Medium (Life Technologies) to N2 Medium (DMEM/F12 medium with N2 supplement, Life Technologies). Cells were cultured in N2 Medium until day 7, dissociated using Accutase (Sigma-Aldrich) and replated ($3 \times 10^5$ cells per $cm^2$) on dishes pre-coated with poly-D-Lysine (1 μg/ml) and laminin (1 μg/ml) using neuron culture medium (Neurobasal Medium with B27 supplement, BDNF (brain-derivd neurotrophic factor, 20 ng/ml, PeproTech), GDNF (Glial cell line-derived neurotrophic factor, 20 ng/ml, PeproTech), TGFβ3 (transforming growth factor type β3, 1 ng/ml, R&D), ascorbic acid (0.2 mM, Sigma-Aldrich), dibutyryl cAMP (0.5 mM, Sigma-Aldrich), and DAPT (10 μM, Stemgent)). From Day 8 to Day 36, half of the cell culture medium was replenished every 3-4 days. For Atoh1-induced DA neuron differentiation protocol, the protocol above was modified by adding SHH (SHH C25II, 100 ng/ml, R&D) and FGF8b (100 ng/ml, PeproTech) from Day 1 to 5.

Atoh1-induced DA neuron precursors at differentiation Day 7 were dissociated using Accutase. $1 \times 10^6$ cells were cryopreserved in 1 ml freezing medium (40% Neurobasal Medium with B27 supplement, 50% fetal bovine serum and 10% DMSO) using a freezing container (Nalgene) in −80° C. for 24 h and stored in liquid nitrogen.

Atoh1-Mediated Differentiation of Human iPSCs into Mature Neurons.

Figure 2A:
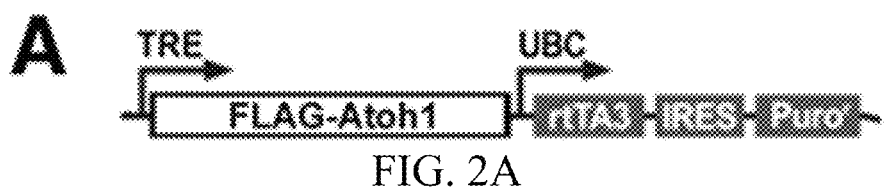
FIG. 2A-2K. Ectopic Atoh1 expression drives neuronal conversion in induced pluripotent stem cells (iPSCs). (A): Diagram of the lentiviral vector for Dox-inducible Atoh1 expression. (B): Dox controls the on/off switch of Atoh1 expression. Human iPSCs were infected with lentivirus harboring Dox-inducible Atoh1. Stable Atoh1-iPSCs after puromycin selection were treated with or without Dox for 48 hours and transferred to Dox-free medium. Whole cell lysates collected on each indicated time point were subjected to immunoblot using anti-FLAG antibody. (C): Atoh1-iPSCs were treated with Dox (+Dox) for 3 days and changed to Dox-free medium (Dox withdrawal) for 3 days. Cells were immunostained with FLAG antibody. (D): Diagram of Atoh1-induced neuron differentiation protocol. Atoh1 is induced by Dox from days 1 to 5. (E): Immunostaining from cell cultures at differentiation day 6 shows TUJ1 expression in Atoh1-induced cells but not in control cells. (F): Brightfield microscope images show cell adhesion and neuronal process formation in Atoh1-induced cells on differentiation day 10. (G): Immunostaining shows the coexpression of TUJ1 and Synapsin in Atoh1-induced neurons on differentiation day 36. (H, I): During a 5-day time period, an equal number of Atoh1-iPSCs received different lengths of Dox treatment (from 1 to 5 days). After being matured for 30 days, cells were immunostained against neuronal marker TUJ1 and MAP2. The percentage of TUJ1+/MAP2+ cells over DAPI+ cells and the total number of TUJ1+/MAP2+ cells were quantified in 10 random-selected microscopic fields (p, p,.01 compared with cells that had 4- and 5-day Atoh1 induction). (J, K): Atoh1-iPSCs were treated with Dox for 2 days and returned to Dox-free medium for 3 days (J). The expression of Atoh1, NEUROD1, and Ngn2 was measured by quantitative real-time polymerase chain reaction in control, Atoh1 induction, and Atoh1 silencing samples (*, p<01 compared with control). In (C) and (E-G), cell nuclei were counterstained with DAPI. Scale bars=20 µm. The data represent means±SEM. Abbreviations: Con, control; DAPI, 4',6-diamidino-2-phenylindole; Dox, doxycycline; FLAG-Atoh1, FLAG-tagged Atoh1; IRES, internal ribosome entry site; Puro$^r$, puromycin selection marker; rtTA3, reverse tet-transactivator; TRE, tet-inducible promoter; UBC, human ubiquitin C promoter.
Figure 2B:
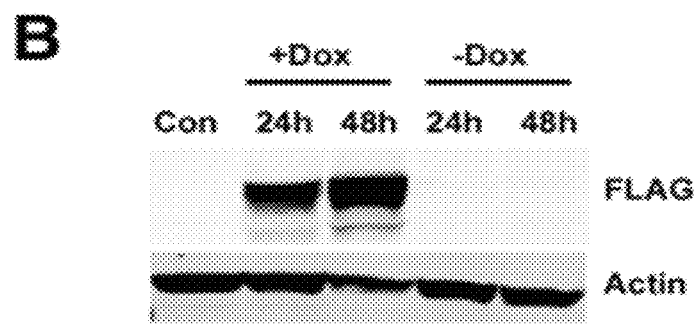
Figure 2C:
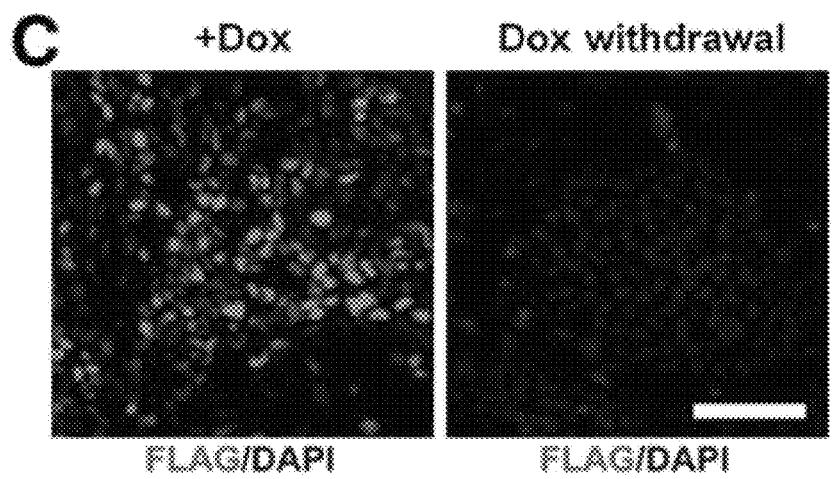
Figure 2D:
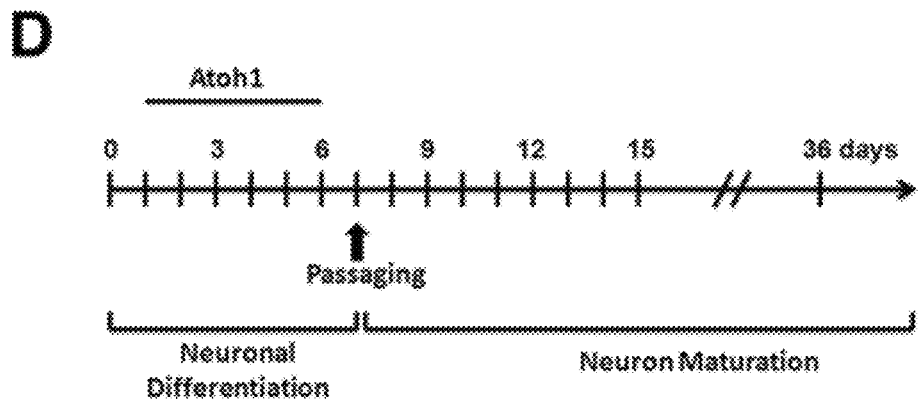

As shown in FIG. 2D, we established protocols for differentiating Atoh1-iPSCs into neurons. The recipes for cell culture media are listed in Table 1. Cells were plated ($4 \times 10^4$ cells per $cm^2$) on matrigel (BD) in Essential 8

Figure 2E:
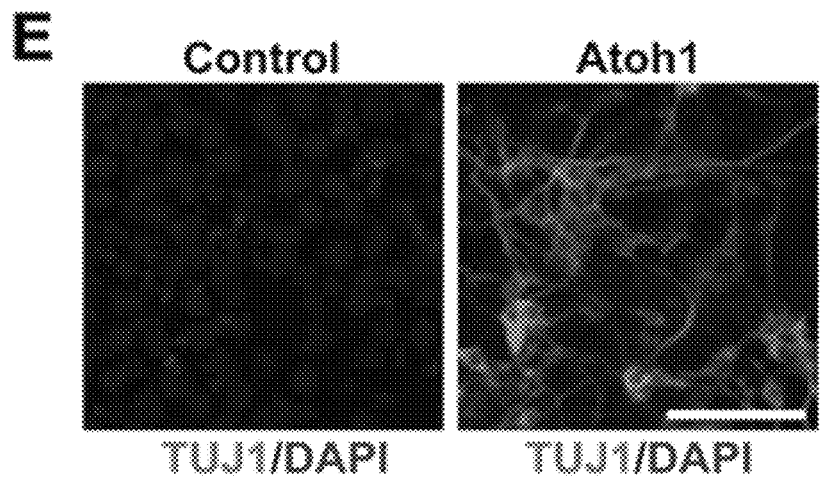
Figure 2F:
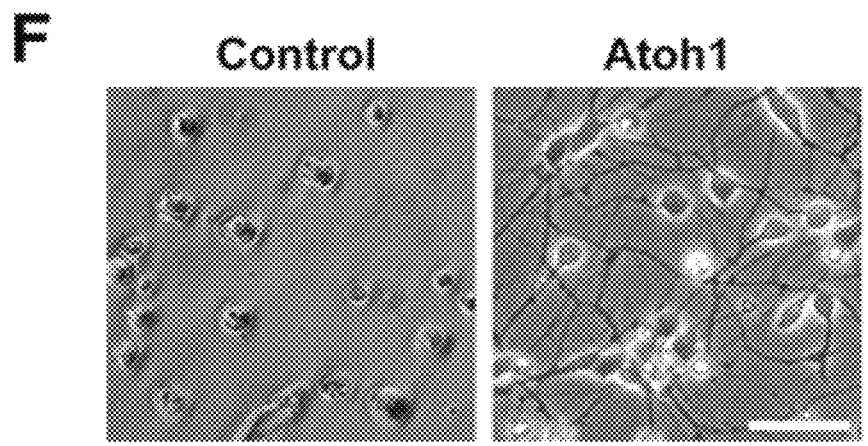
Figure 2G:
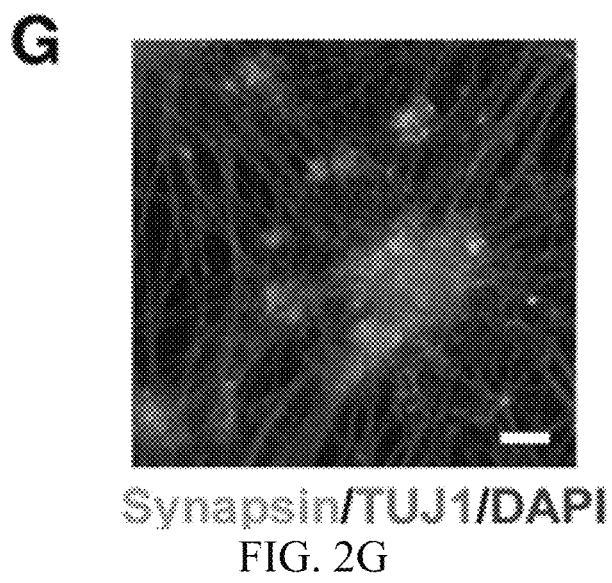

Medium (Life Technologies) with ROCK inhibitor (Y-27632, Stemgent). From Day 1 to Day 7, cell culture medium was changed every day. From Day 8 to Day 36, half of the cell culture medium was changed every 3-4 days. On differentiation day 6, Atoh1 dramatically increases the level of neuronal differentiation marker (TUJ1) when compared with Dox-untreated control (FIG. 2E). On day 7, cells were dissociated using Accutase (Sigma-Aldrich) and replated ($3 \times 10^5$ cells per cm$^2$) on dishes pre-coated with poly-D-Lysine (1 µg/ml) and laminin (1 µg/ml). After cell passaging, cells differentiated by Atoh1 adhered and formed neuronal processes (FIG. 2F, right panel). Cells without Atoh1 induction failed to attach and grow in neuron culture medium (FIG. 2F, left panel). Atoh1-induced neurons further matured in vitro, and co-expressed neuronal marker (β-tubulin III, TUJ1) and synaptic resident protein (synapsin), suggesting the establishment of synaptic terminals and neuronal maturation (FIG. 2G).

TABLE 1

Neuron differentiation media used in Atoh1-induced protocol as shown in FIG. 2D

| Day | Medium | Additives |
|---|---|---|
| 0 | E8 | Y-27632 |
| 1 | E6 (75%) + N2 (25%) | Doxycyline |
| 2 | E6 (50%) + N2 (50%) | Doxycyline |
| 3 | E6 (25%) + N2 (75%) | Doxycyline |
| 4 | N2 | Doxycyline |
| 5 | N2 | Doxycyline |
| 6 | N2 (50%) + B27 (50%) | |
| 7 | B27 | |
| 8-36 | B27 | B/G/C/A/D |

E8: Essential 8 Medium
E6: Essential 6 Medium
N2: DMEM/F12 medium with N2 supplement (1:100)
B27: neurobasal medium with B27 supplement (1:50)
Doxycyline (0.5 µg/ml)
Y-27632 (10 µM)
B/G/C/A/D: BDNF (20 ng/ml)/GDNF (10 ng/ml)/Dibutyryl cAMP (0.5 mM)/Ascorbic Acid (0.2 mM)/DAPT (10 µM)

Quantitative Real-Time PCR (qRT-PCR).

Total RNA was extracted using the RNeasy Mini kit (Qiagen). Reverse transcription was performed using MuLV reverse transcriptase (Applied biosystems) and Oligo(dT) primers. qRT-PCR was performed using SYBR Green PCR Master Mix (Applied Biosystems) and IQ5 RT-PCR detection system (Bio-rad). All primer sequences are listed in Table 1. Relative expression of each gene was normalized to the 18S rRNA.

Western Blot.

Total cellular proteins were extracted with RIPA buffer (Sigma-Aldrich) containing a protease and phosphatase inhibitor cocktail (Calbiochem). SDS-PAGE was performed with 50 µg total cellular proteins per lane using 4-12% gradient Tris-glycine gels (Lonza). Western blot was performed using Quantitative Western Blot System (LI-COR Biosciences) following the manufacturer's instructions. The primary antibodies were: mouse anti-FALG M2 (Sigma-Aldrich), rabbit anti-Atoh1 (Millipore) and mouse anti-β-actin (Sigma-Aldrich). Secondary antibodies were labeled with IRDye infrared dyes and protein levels were quantified with Odyssey Infrared Imaging System (LI-COR Biosciences).

Immunofluorescence and Cell Counting.

Differentiated cells were fixed in 4% PFA/1% sucrose in PBS (pH 7.4) at room temperature, and blocked with 5% normal goat serum and 0.2% Triton X-100. Primary antibodies (Table 2) were diluted in 5% normal goat serum and incubated with samples overnight at 4° C. Cy3 and Alexa 488 labeled secondary antibodies were applied for 2 hours. Samples were counterstained with DAPI and mounted on glass slides using ProLong anti-fade kit (Life Technologies).

The percentage of marker positive cells was determined in samples derived from at least three independent experiments. In Adobe Photoshop software, images from 10 randomly selected fields were used for counting the number of DAPI-positive cells expressing a specific marker.

Electrophysiological Recordings.

Voltage-clamp or current-clamp recordings were performed at 35° C. in a chamber perfused with regular Artificial Cerebrospinal Fluid (ACSF; in mM: NaCl, 124; KCl, 2.5; MgCl$_2$, 1.3; CaCl$_2$ 2.5; NaH$_2$PO$_4$, 1; NaHCO$_3$, 26.2; glucose, 20; pH 7.4, equilibrated with 95% O$_2$ and 5% CO$_2$, ~310 mosm) which flowed at 4 ml/min. Patch electrodes were pulled from borosilicate glass and had resistances of 2-4.0 MΩ when filled with an intracellular solution (in mM: KMeSO$_4$, 135; KCl, 5; HEPES, 5; EGTA free acid, 0.25; Mg-ATP, 2; GTP, 0.5; phosphocreatine-tris, 10; pH 7.3, ~290 mosm).

Neurons were identified using a 10× objective mounted on an upright microscope with transmitted light, and their neuronal somata were then visualized through a 40× water immersion objective using infrared differential interference contrast (DIC) optics. The cell somatic recordings were made using an Axopatch 200B amplifier in combination with pClamp 9.0 software (Molecular Devices). Neurons were voltage-clamped at −80 mV. $R_{series}$ and $R_{input}$ were monitored using a 2.5 mV 100 ms depolarizing voltage step in each recording sweep. Current traces were filtered at 5 kHz, and digitized at 10 kHz using a Digidata 1322A interface, and stored for off-line analysis. Leak and capacitative currents were corrected by subtracting a scaled current elicited by a +2.5 mV step from the holding potential.

For current clamp recording, the same Axopatch 200B amplifier was used; whole cell mode was achieved initially in the voltage clamp configuration. Then, the recording was switched into current clamp mode. The resting membrane potential was monitored for more than five minutes. The experiment was discontinued if the resting membrane potential became more positive than −40 mV. The action potential was continually monitored for five minutes, and if there was no threshold change, the reagent perfusion commenced. All reagents were bought from Sigma (St Louis, Mo.) except TTX (abcam, Cambridge, Mass.) and ML252 (Vanderbilt Center for Neuroscience Drug Discovery).

High-Performance Liquid Chromatography (HPLC) Analysis.

On day 36 of differentiation, medium was replaced by HBSS buffer with addition of 56 mM KCl (200µl per well in 24-well plates) and incubated for 15 min at 37° C. Medium was collected and centrifuged (15,000 g for 15 min at 4° C.) to clear cell debris. Samples were immediately frozen in liquid nitrogen and stored at −80° C. For HPLC analysis, samples were thawed and concentrated using a vacuum (Savant SDP 121P ThermoSci) connected with refrigerated vapor trap (Savant RVT 5105 ThermoSci) and the freeze dried samples were resuspended in 10 mM perchloric acid. Monoamines were analyzed by HPLC-ECD (Electrochemical Detection) by dual channel coulchem III electrochemical detector (Model 5300, ESA, Inc. Chelmsford, Mass., USA), and monoamines were separated by using a reverse phase C18 column (3 mm×150 mm C-18 RP-column, Acclaim Polar advantage II, Thermo Scientific) with a flow rate of 0.600 mL/min. Monoamine concentrations were quantified by comparison of the area under the curve (AUC) to known standard dilutions.

6-OHDA Treatment in DA Neurons and LDH Analysis

Neuron culture medium was changed to neurobasal medium before treatment. 6-OHDA was freshly prepared in vehicle solution (ascorbic acid (0.15%) in $H_2O$) and quickly added to the neuron culture. Control cells were treated with vehicle solution alone. After 15 min at 37° C., the medium was removed and neurons were gently washed twice with Neurobasal Medium. 200 μl neuron culture medium (Neurobasal Medium with B27 Supplement) was added to each well and further incubated for 24 h. Cytotoxicity induced by 6-OHDA was measured using LDH Cytotoxicity Detection Kit (Roche) following the manufacturer's protocol. The percentage cytotoxicity was calculated using the following equation: Cytotoxicity (%)=(Experiment Value−Low Control)/(High Control−Low Control)×100. (Low control: culture medium; High control: total cell lysate).

Data Analysis and Statistics.

All results reported here represent at least three independent replications. Statistical analysis was performed using Prizm software (GraphPad). Post-hoc tests included the Students t-test and the Tukey multiple comparison tests as appropriate. All data are represented as mean value±standard error of mean (SEM).

For neurophysiological recordings, the recorded data were first visualized with Clampfit 9.2, and exported to Matlab (Mathworks, Natick, Mass.) for further analysis and plotting. The recording traces are visualized with Igor 6.0 (WaveMetrics, Portland, Oreg.). All group data are reported as mean±STD except otherwise stated.

Results

Atoh1 is Induced During the Neuronal Differentiation of Human PSCs.

Figure 1B:
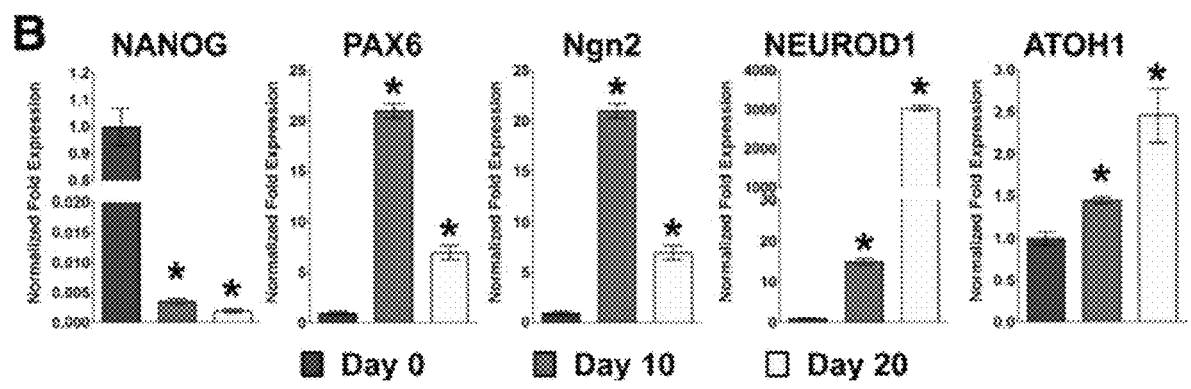
Figure 1C:
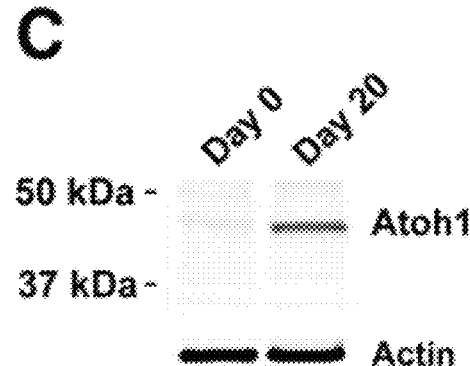

We followed a dual-SMAD inhibition protocol (Chambers et al., 27 NAT. BIOTECHNOL. 275-80 (2009)) for differentiating human iPSCs into neurons. Differentiated cells first expressed neurectodermal marker (PAX6) and neural rosette marker (NESTIN) at day 10 of differentiation (FIG. 1A, left). Mature neurons at day 40 of differentiation expressed neuronal marker β-Tubulin III (TUJ1) and MAP2 (FIG. 1A, right). We further examined the expression of various markers at differentiation day 0, 10 and 20 by quantitative real-time PCR (qRT-PCR), which confirmed the inhibition of pluripotency marker (NANOG) and the induction of neural markers (PAX6, Ngn2 and NEUROD1) (FIG. 1B). Next, we examined Atoh1 expression by qRT-PCR and found that ATOH1 was induced at differentiation day 10 and 20 when compared to undifferentiated cells (FIG. 1B). Western blotting also confirmed the induction of Atoh1 protein at differentiation day 20 (FIG. 1C). These data suggested that Atoh1 is involved in the neuronal conversion of human PSCs, which warranted further study.

Ectopic Atoh1 Expression Induces Highly Efficient Neuronal Conversion of Human PSCs.

To address whether Atoh1 induction is sufficient for the neuronal differentiation of human PSCs, we established a lentivirus-mediated gene delivery system to achieve Dox-inducible Atoh1 expression in human PSCs. We constructed a Tet-On lentiviral vector that harbors human Atoh1 transgene with N-terminal FLAG tag (SEQ ID NO:3) (FIG. 2A). Human iPSCs and ESCs were infected with Atoh1 lentivirus to establish stable cell lines (Atoh1-iPSC, and Atoh1-ESC) after puromycin selection. Dox treatment for 48 h in Atoh1-iPSCs induced Atoh1 expression as determined by immunoblotting against FLAG tag, and transgenic Atoh1 expression was turned off after Dox withdrawal (FIG. 2B). Immunostaining against FLAG tag also confirmed Atoh1 induction after 3-day Dox treatment and the silencing of Atoh1 transgene after Dox withdrawal for 3 days (FIG. 2C).

Figure 8:
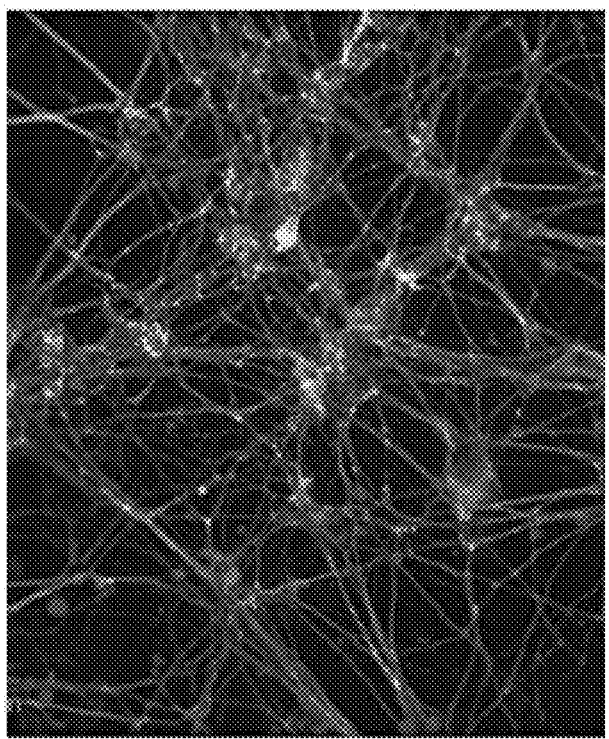
FIG. 8. Neuronal maturation of Atoh1-induced neurons derived from human ESCs. At differentiation day 36, Atoh1-induced neurons derived from ESCs co-expressed the synaptic vesicle protein Synapsin and neuronal marker TUJ1. Cell nuclei were counterstained with DAPI. Bar: 20 µm.

Next, we induced ectopic Atoh1 expression in PSCs for neuronal differentiation following a protocol outlined in FIG. 2D (also see details in Materials and Methods). Atoh1-iPSCs were maintained in a feeder-free culture system, and Atoh1 was induced by Dox for 5 days to drive neuronal conversion. After Dox withdrawal, neuronal precursors were passaged and allowed to further mature in vitro. On differentiation day 6, Atoh1 induced robust expression of the neuronal differentiation marker TUJ1, which was not detected in Dox-untreated cells (FIG. 2E). On day 7, cells were dissociated and replated on surfaces pre-coated for neuron culture. Two days after cell passaging, Atoh1-induced cells adhered and formed neuronal processes. In contrast, control cells failed to attach or grow in neuron culture medium (FIG. 2F). After further maturation in vitro for 30 days, Atoh1-induced neurons co-expressed the synaptic vesicle protein Synapsin and neuronal marker (TUJ1), demonstrating the establishment of synaptic terminals and neuronal maturation (FIG. 2G). We also replicated these results in Atoh1-ESC, in which Atoh1 also initiated the neuronal differentiation process and generated mature neurons (FIG. 8).

Figure 2H:
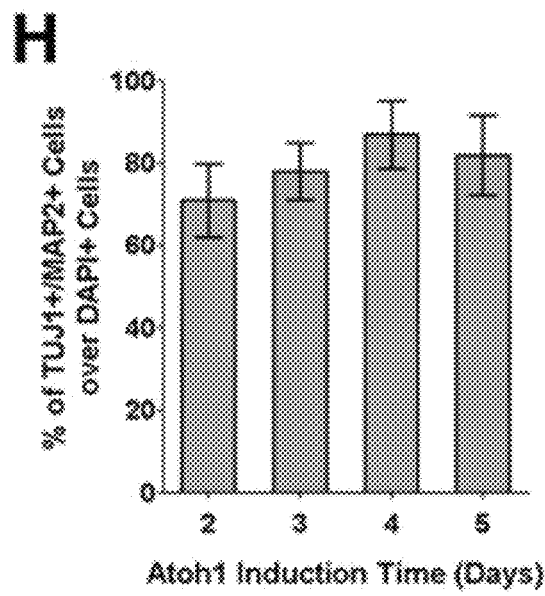
Figure 2I:
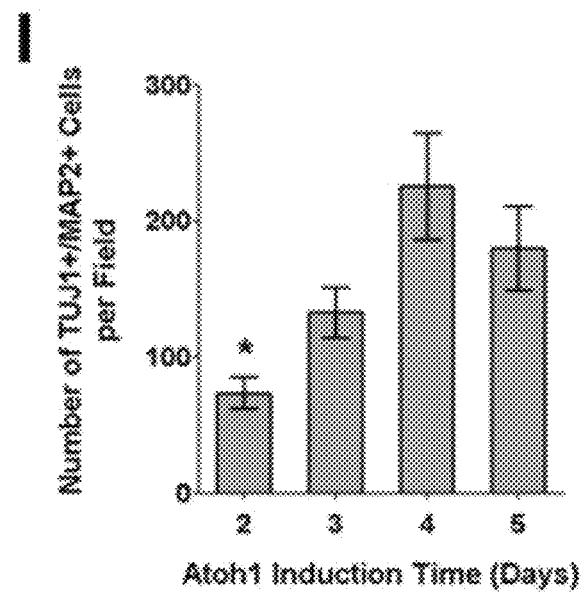
Figure 2J:
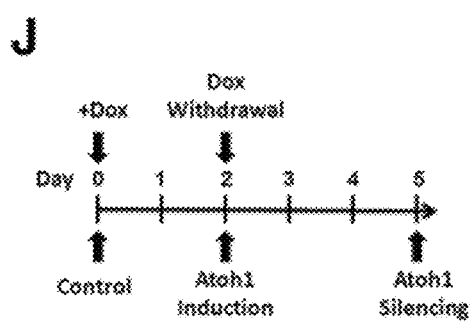
Figure 2K:
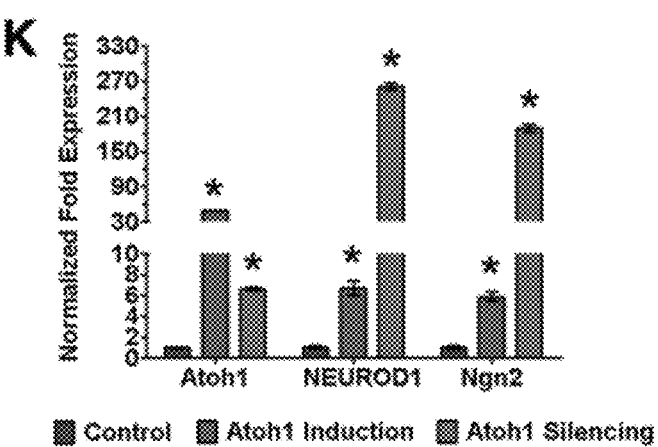
Figure 9:
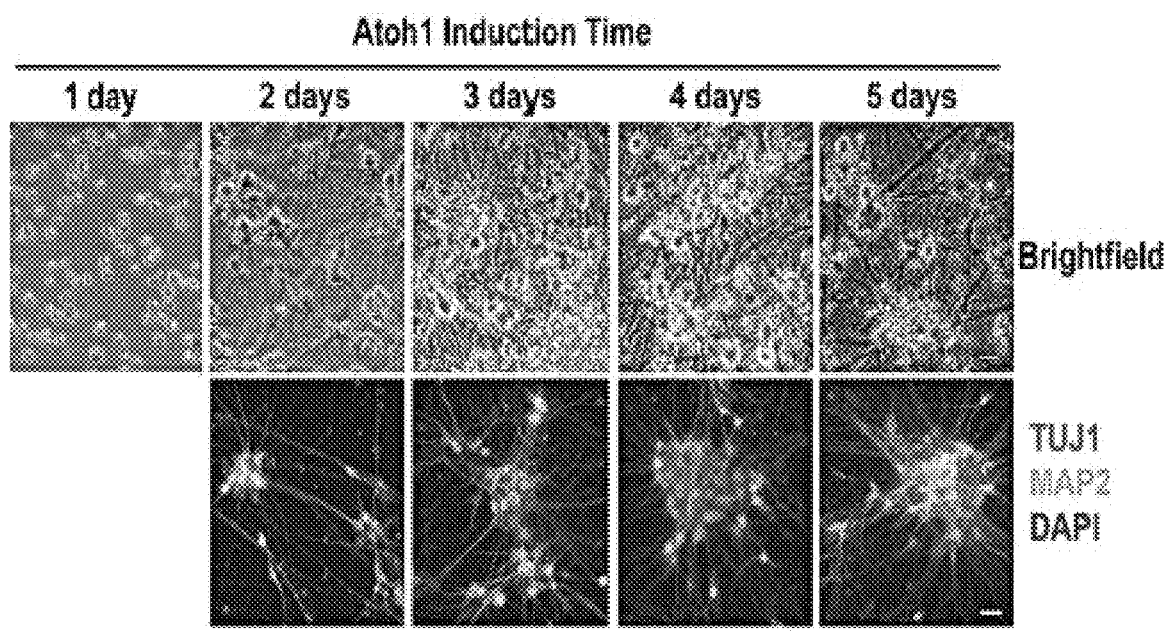
FIG. 9. Atoh1 induction for 2-5 days is sufficient for neuronal conversion in iPSCs. During a 5-day time period, equal number of Atoh1-iPSCs received different length of Dox treatment (from 1 to 5 days). Brightfield microscope images show neurons at differentiation day 36, which were also immunostained against neuronal marker TUJ1 and MAP2. Cell nuclei were counterstained with DAPI. Bar: 20 µm.

To further optimize the Atoh1-mediated differentiation strategy, we asked what is the minimum time of Atoh1 induction for successful neuronal conversion. Equal numbers of Atoh1-iPSCs received different durations of Dox treatment (1 to 5 days), after which cells were replated and allowed to mature in vitro for additional 30 days. Cells with Dox treatment for 1 day failed to attach after replating. In contrast, Dox treatment for 2 to 5 days successfully differentiated iPSCs into neurons expressing TUJ1 and MAP2 (FIG. 9). By quantifying the number of TUJ1+/MAP2+ neurons, we found that longer Atoh1 induction time did not increase the purity of Atoh1-induced neurons (FIG. 2H), but did significantly increase the yield of neurons, especially when comparing Atoh1 induction for 4-5 days to 2-day induction (FIG. 2I). To compare the level of neurogenic signaling before and after silencing ectopic Atoh1 expression, we treated Atoh1-iPSCs with Dox for 2 days and then withdrew Dox for 3 days (FIGS. 2J and 2K). As determined by qRT-PCR, Atoh1 showed 49-fold up-regulation after Dox treatment and decreased after Dox withdrawal. Two neurogenic transcription factors (NEUROD1 and Ngn2) showed 6- and 5-fold induction, respectively, in response to Atoh1 induction. After Dox withdrawal, their expression did not decrease but increased further to 261- and 189-fold higher than control cells, respectively. These results suggest that ectopic Atoh1 expression in PSCs initiates a neurogenic program that becomes self-sustaining after the withdrawal of ectopic Atoh1.

Figure 3A:
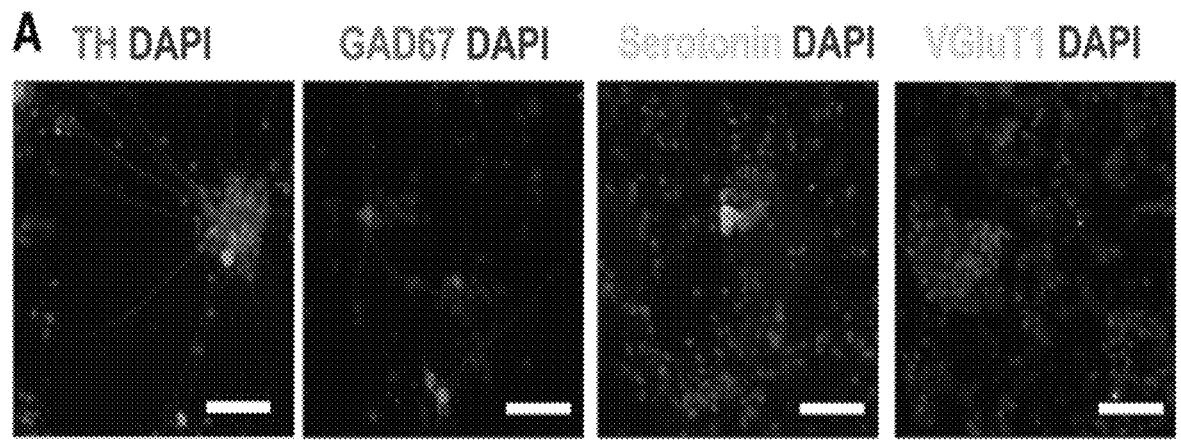
FIG. 3A-3B. Neuron subtype specification in Atoh1-induced neurons. (A): Atoh1-induced neurons derived from Atoh1-induced pluripotent stem cells were allowed to mature in vitro, and cells at differentiation day 36 were immunostained with antibodies detecting dopaminergic (TH), GABAergic (GAD67), serotonergic (serotonin), and glutamatergic (VGluT1) neuron subtypes. Cell nuclei were counterstained with DAPI. Scale bars=50 µm. (B): Immunostained neurons from 10 random-selected microscopic fields were counted to calculate the percentage of TH+, GAD67+, serotonin+, and VGluT1+ cells over DAPI+ cells. The data represent means±SEM. Abbreviations: DAPI, 4',6-diamidino-2-phenylindole; N.D., not detected; TH, tyrosine hydroxylase; VGluT, vesicular glutamate transporter 1.
Figure 3B:
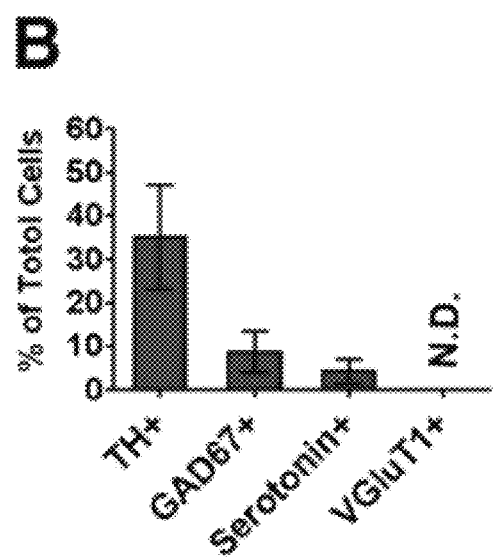

To determine the subtype specification of Atoh1-induced neurons, we characterized neurons induced from Atoh1-iPSCs with various neuron subtype markers (FIG. 3). By day 36 of differentiation, ~35% of Atoh1-induced neurons expressed tyrosine hydroxylase (TH), the rate-limiting enzyme in DA synthesis and a widely-used DA neuron marker. Fewer than 10% of total cells expressed glutamate decarboxylase (GAD67) and serotonin, markers for GABAergic and serotonergic neurons, respectively. Glutamatergic neurons expressing Vesicular Glutamate Transporter 1 (VGluT1) were not detected in Atoh1-induced neurons.

Atoh1-Mediated Differentiation of Human PSCs into DA Neurons.

Figure 4A:
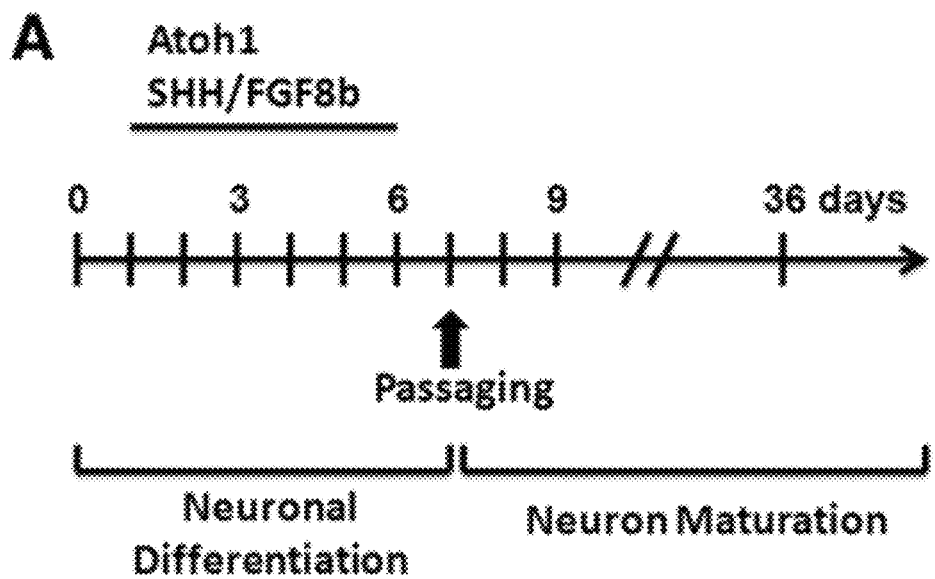
FIG. 4A-4F. Ectopic Atoh1 expression and cell extrinsic factors induce dopaminergic (DA) neurons from PSCs. (A): Diagram of DA neuron differentiation induced by Atoh1, SHH, and FGF8b. (B): Atoh1-iPSCs were differentiated by Atoh1 induction alone or in combination with SHH and FGF8b. The expression of DA lineage markers was analyzed by quantitative real-time polymerase chain reaction using cells at differentiation day 6. Control cells followed the same differentiation protocol but did not receive Dox treatment. Atoh1 induction in combination with SHH and FGF8b more robustly induced DA lineage markers than Atoh1 alone or untreated cells. The data represent means±SEM. *, p<01 compared with Atoh1 alone; ♦, p<01 compared with control. (C, D): Atoh1-iPSCs were differentiated following the protocol shown in (A). Atoh1-induced neurons at differentiation day 36 were immunostained for neuronal marker (TUJ1) and DA neuron marker (TH). Cell nuclei were counterstained with DAPI. Scale bars=20 TH+/TUJ1+DA neurons derived from Atoh1-iPSCs and Atoh1-ESCs from 10 random-selected microscopic fields were counted to calculate the percentage of TH+/TUJ1+ cells over DAPI+ cells. The data represent means±SEM. (E): Bright-field microscope image of Atoh1-induced iPSC-derived DA neurons 7 days after being recovered from cryopreservation. Scale bars=20 (F): Atoh1-iPSCs (1×10$^6$) were differentiated following the protocol shown in (A). Cells were counted to calculate the number of NPCs (differentiation day 7), DA neurons (differentiation day 14), and post-thaw DA neurons (frozen at differentiation day 7 and cultured 7 days after cryopreservation). Abbreviations: Atoh1+S/F, Atoh1 induction in combination with SHH and FGF8b; DAPI, 4',6-diamidino-2-phenylindole; DAT, dopamine transporter; ESC, embryonic stem cell; FGF, fibroblast growth factor; iPSC, induced pluripotent stem cell; NPC, neuron precursor cell; SHH, Sonic Hedgehog; TH, tyrosine hydroxylase.
Figure 4B:
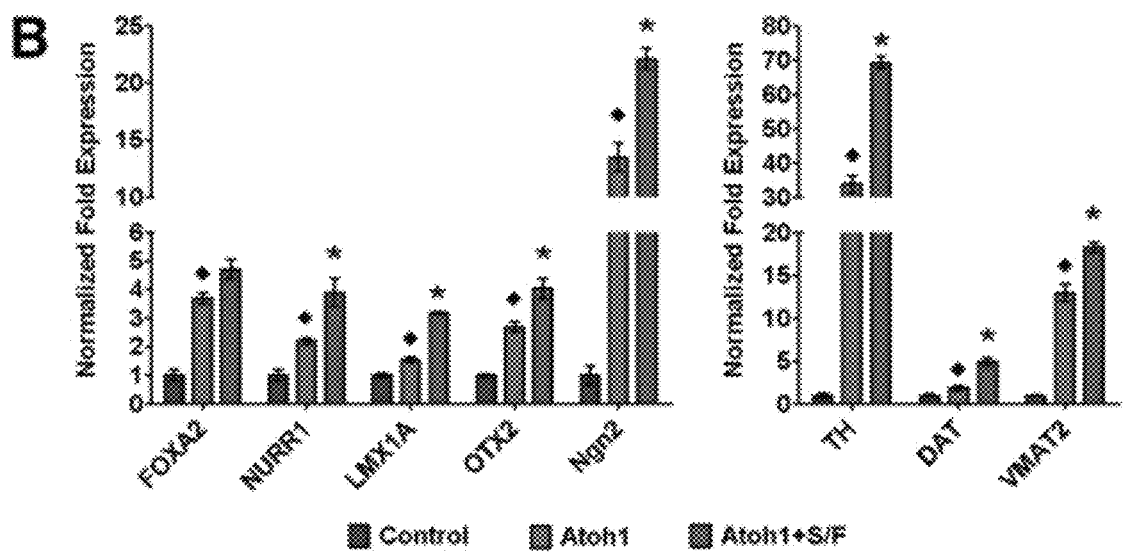
Figure 4C:
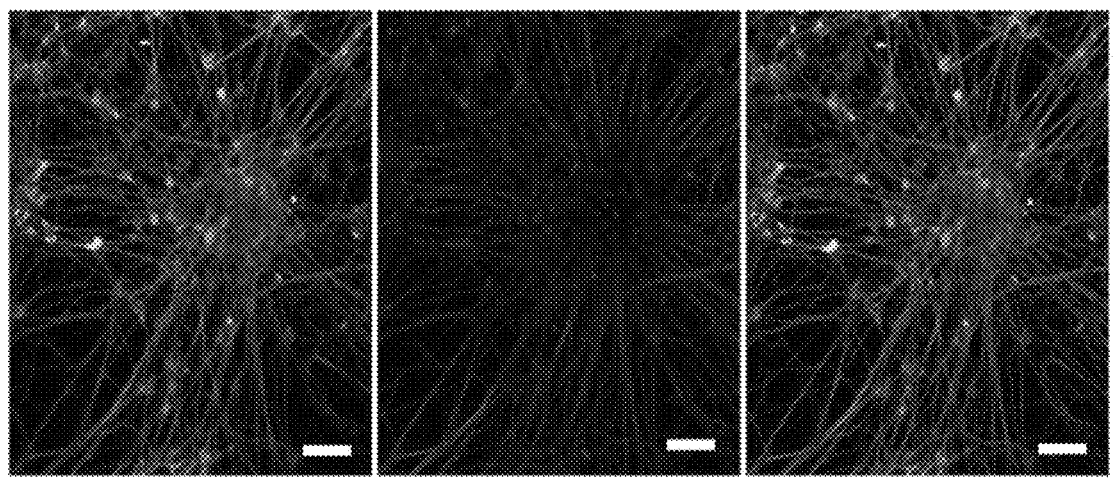
Figure 4D:
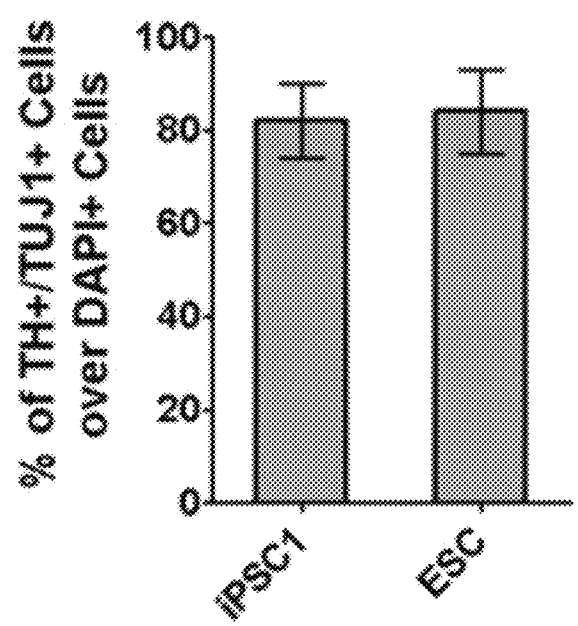
Figure 10:
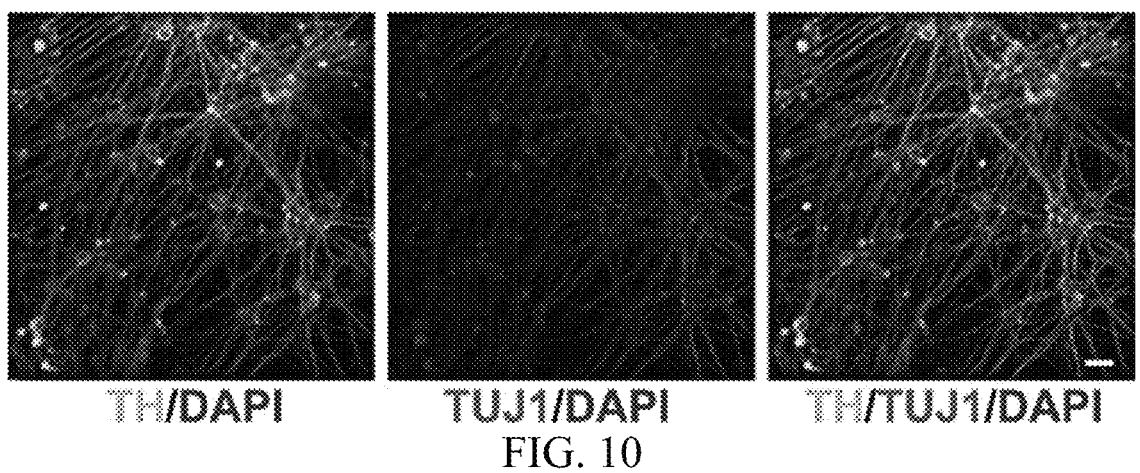
FIG. 10. Atoh1-induced DA neurons from human ESCs at differentiation day 36 were immunostained with neuronal marker (TUJ1) and DA neuron marker (TH). Cell nuclei were counterstained with DAPI. Bar: 20 µm.

We found that ectopic Atoh1 expression preferentially drives the differentiation of human PSCs to TH-expressing neurons, suggesting a DA lineage specification. Two morphogens (SHH and FGF-8b) for neural patterning have been widely used to drive DA lineage specification during the neuronal conversion of human PSCs. We combined Atoh1 induction with these two morphogens to differentiate PSCs into DA neurons, following a protocol outlined in FIG. 4A. Ectopic Atoh1 expression alone induced multiple DA neuron markers, such as FOXA2, NURR1, LMX1A, OTX2, Ngn2, TH, DAT and VMAT2, most of which were further upregulated significantly by combining Atoh1 induction with SHH and FGF-8b (FIG. 4B). At day 36 of differentiation, Atoh1-induced neurons derived from both iPSCs and ESCs co-expressed the neuronal marker (TUJ1) and the DA neuron marker (TH) (FIG. 4C and FIG. 10). The Atoh1-mediated protocol yielded DA neurons from human iPSCs and ESCs with 82±8% and 84±9% purity, respectively, as determined by the percentage of TH+/TUJ1+ cells over DAPI+ cells (FIG. 4D).

Figure 4E:
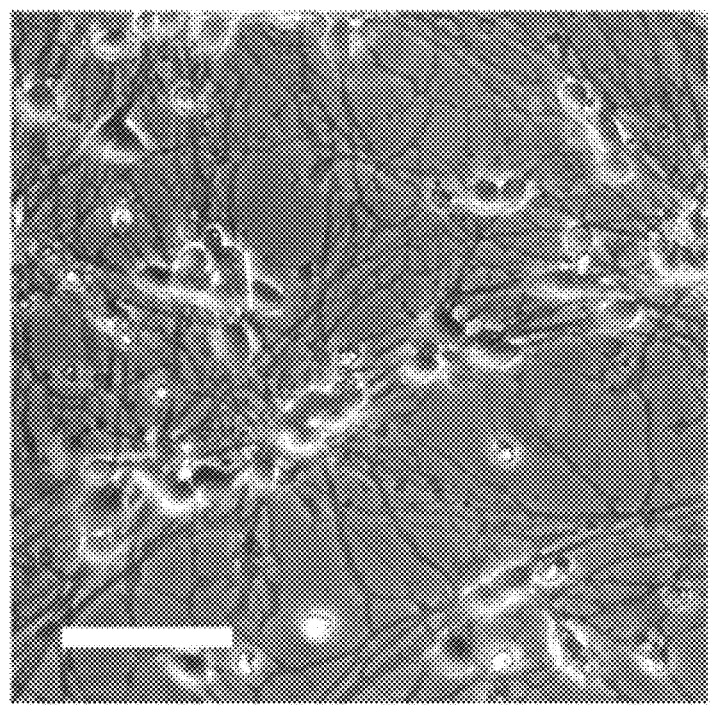
Figure 4F:
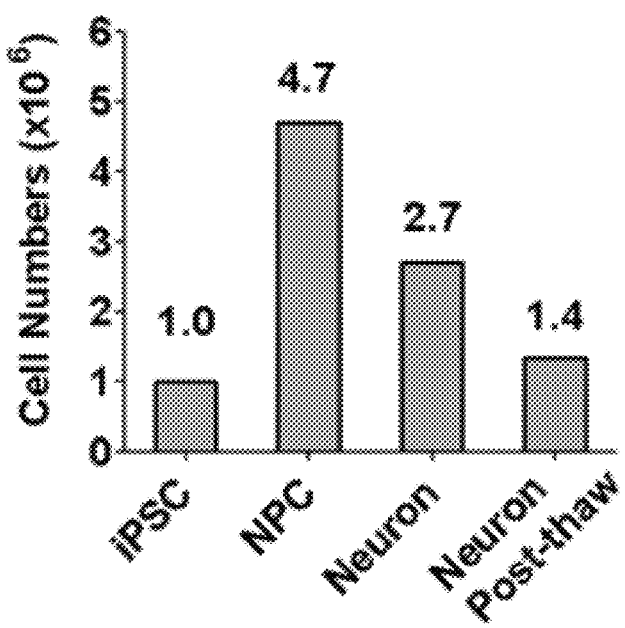

In order to store Atoh1-induced DA neurons, Atoh1-induced DA neuron precursor cells (NPCs) at differentiation day 7 were cryopreserved, and these cells showed high viability and neuronal morphology when being recovered from cryopreservation and cultured for 7 days (FIG. 4E). From $1 \times 10^6$ iPSCs, the Atoh1-mediated protocol generated $4.7 \times 10^6$ DA NPCs, and yielded $2.7 \times 10^6$ or $1.4 \times 10^6$ DA neurons after direct cell passaging or cryopreservation, respectively (FIG. 4F).

Figure 5A:
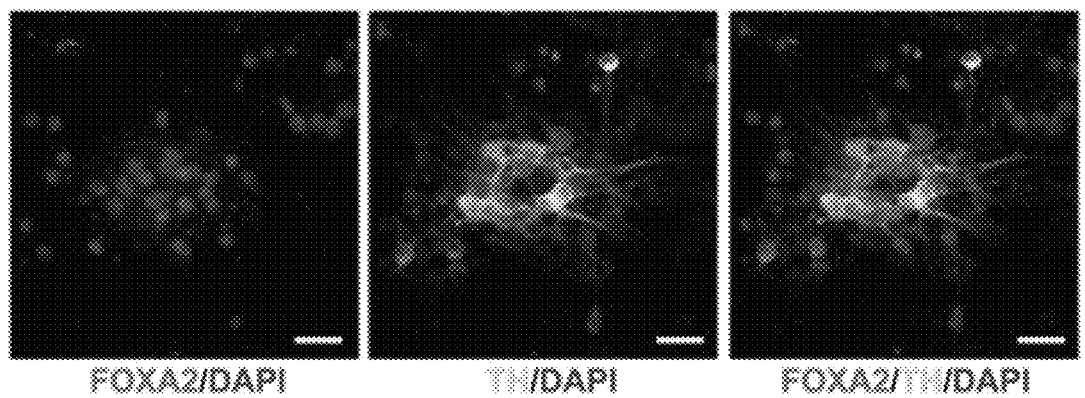
FIG. 5A-5G. The expression of midbrain DA neuron markers and dopamine release in Atoh1-induced neurons. (A-E): Atoh1-induced pluripotent stem cells were differentiated following the protocol shown in FIG. 4A. DA neurons at differentiation day 36 were immunostained for midbrain DA neuron markers (FOXA2, NURR1, EN1, TH, GIRK2, and DAT) and mature neuron marker (Synapsin). Cell nuclei were counterstained with DAPI. The arrows and arrowhead in (E) indicate DAT+ and DAT− neurons, respectively. Scale bars=20 (F, G): Representative HPLC chromatogram (F) and quantification (G) of DA and its metabolites (DOPAC, 3-MT, and HVA) released from Atoh1-induced DA neurons at differentiation day 36 in response to KCl-evoked depolarization for 15 minutes. The data represent means±SEM (n=2). Abbreviations: DA, dopaminergic; DAPI, 4',6-diamidino-2-phenylindole; DAT, dopamine transporter; DOPAC, 3,4-dihydroxy-phenylacetic acid; GIRK2, G protein-regulated inward-rectifier potassium channel 2; HVA, homovanillic acid; 3-MT, 3-methoxytyramine; TH, tyrosine hydroxylase.
Figure 5B:
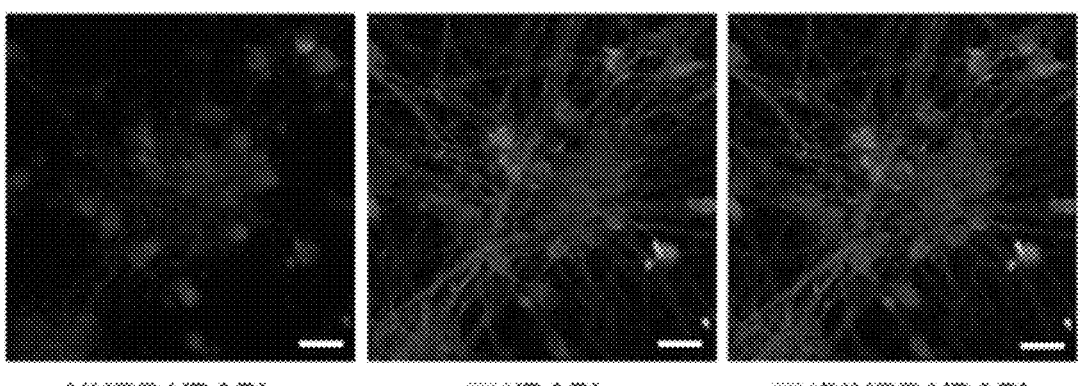
Figure 5C:
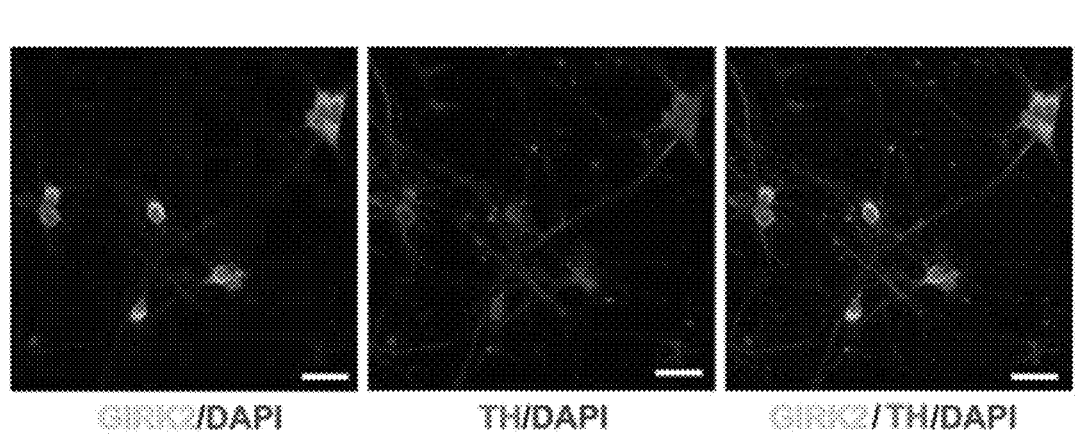
Figure 5D:
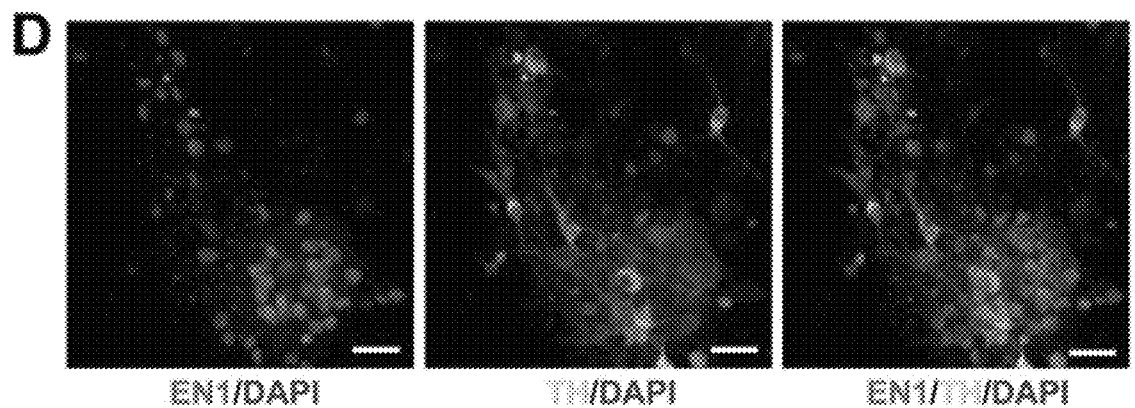
Figure 5E:
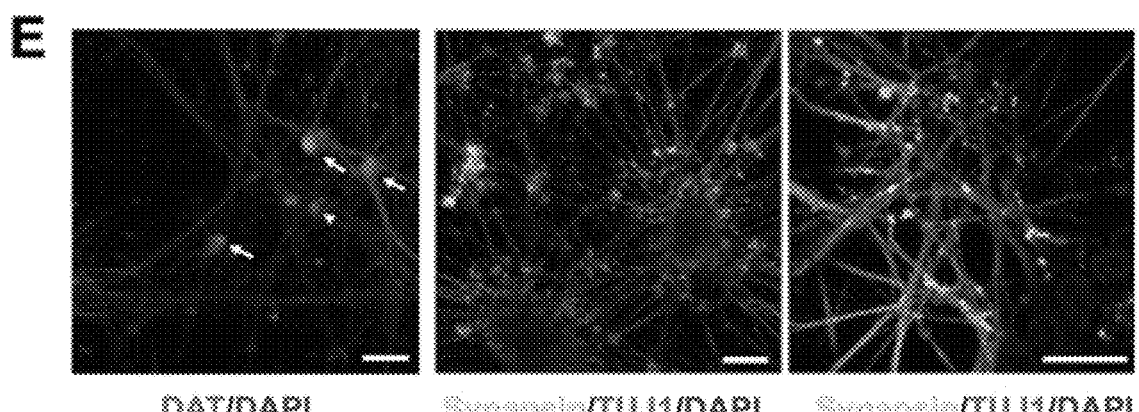
Figure 11:
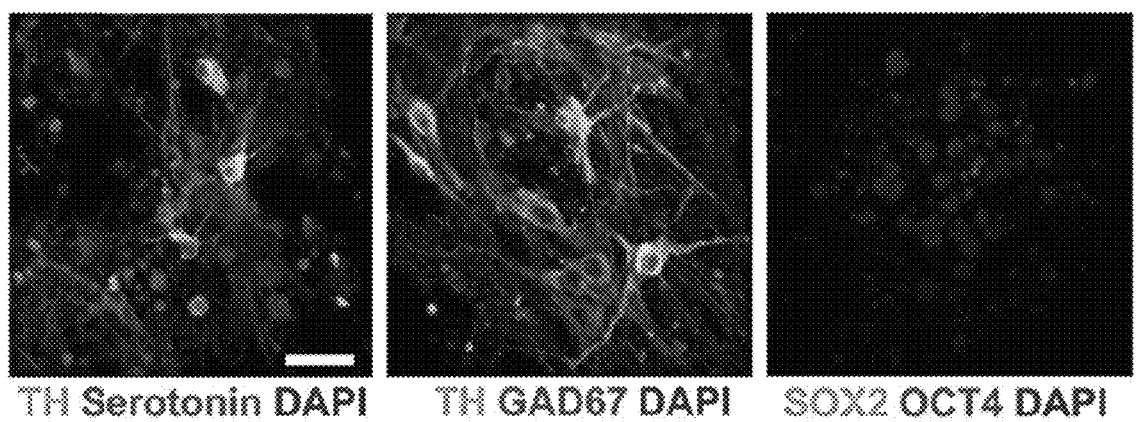
FIG. 11. Atoh1-induced DA neurons from human iPSCs at differentiation day 36 were immunostained against GAD67, serotonin, SOX2 and OCT4. Cell nuclei were counterstained with DAPI. Bar: 20 µm.

Next, we analyzed the expression of midbrain DA neuron markers in Atoh1-induced neurons. By differentiation day 36, these neurons expressed the midbrain DA neuron markers FOXA2, NURR1, Engrailed 1 (EN1), TH, G-protein-regulated inward-rectifier potassium channel 2 (GIRK2) and dopamine transporter (DAT) (FIGS. 5A, 5B, 5C, 5D and 5E), which are also expressed in midbrain DA neurons located in substantia nigra pars compacta (SNpc). These Atoh1-induced DA neurons show extensive TUJ1+ nerve fiber growth and robust expression of synaptic vesicle protein Synapsin (FIG. 5E). GABAergic (GAD67+) or serotonergic (serotonin+) neurons were not detected in Atoh1-induced neurons derived from iPSCs, and undifferentiated iPSCs (SOX2+ or OCT4+) were also not detected (FIG. 11).

Functional Characterization of Atoh1-Induced DA Neurons.

Figure 5F:
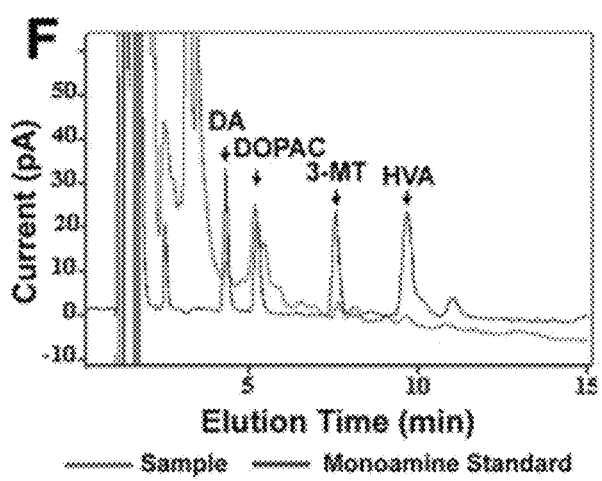
Figure 5G:
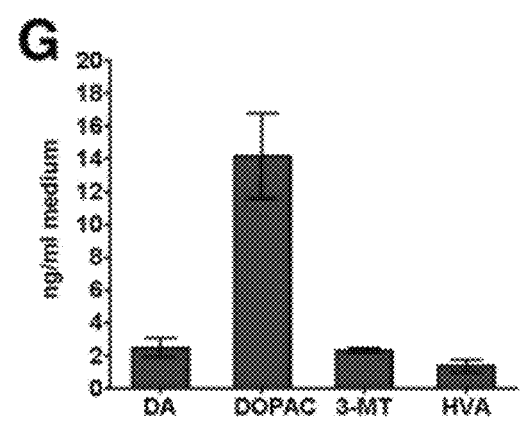

We asked if Atoh1-induced DA neurons exhibit key physiological properties of mature midbrain DA neurons. Dopamine release was quantified in Atoh1-induced DA neurons at differentiation day 36. HPLC analysis demonstrated the release of dopamine and its metabolites evoked by KCl depolarization (FIGS. 5F and 5G).

Figure 6A:
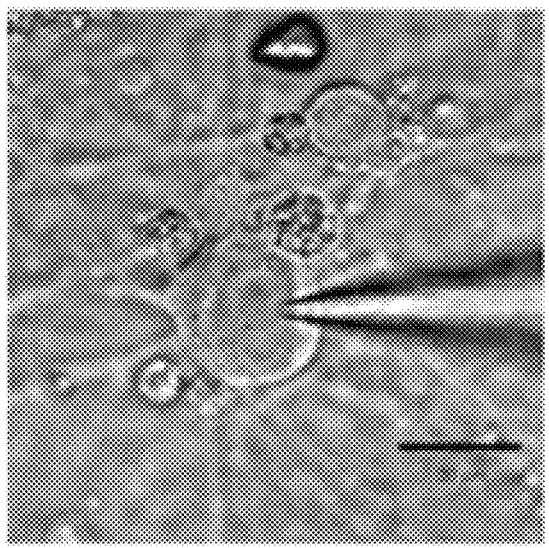
FIG. 6A-6D. Electrophysiological properties of Atoh1-induced dopaminergic (DA) neurons. (A): Differential interference contrast image of a patched Atoh1-induced DA neuron. Scale bar=20 µm. (B, C): Atoh1-induced DA neurons derived from Atoh1-iPSCs showed spontaneous spiking activity. This cell has a resting membrane potential of 265 mV (B) (a zoomed view is shown in the right panel) and an average spiking frequency of 4.8 Hz (C) (left panel). The spontaneous spiking frequencies from 37 neurons were plotted in the right panel of (C) with the means6 SEM marked inside. (D): Whole cell current-clamp recording of action potentials evoked by 70 pA current injection (top panel). Action potentials were suppressed by sodium channel blocker (TTX) (middle panel). Action potentials recovered after TTX withdrawal (bottom panel). (E): An hyperpolarized injection of current (0.2 nA) evoked hyperpolarization and rebound tonic spiking. A typical hyperpolarization sag was observed in the upper panel, which was dampened by ML252 (5 mM, a KCNQ2 inhibitor, lower panel). (F): Voltage-clamp recording of Atoh1-induced neurons. Depolarized sodium and potassium currents were evoked by elevation the membrane potential to different levels (left panel). Both sodium and potassium currents were attenuated by sodium and potassium channel inhibitors (TTX [0.5 mM] and 4-AP [25 mM], respectively). Abbreviations: ACSF, artificial cerebrospinal fluid; TTX, tetrodotoxin.
Figure 6B:
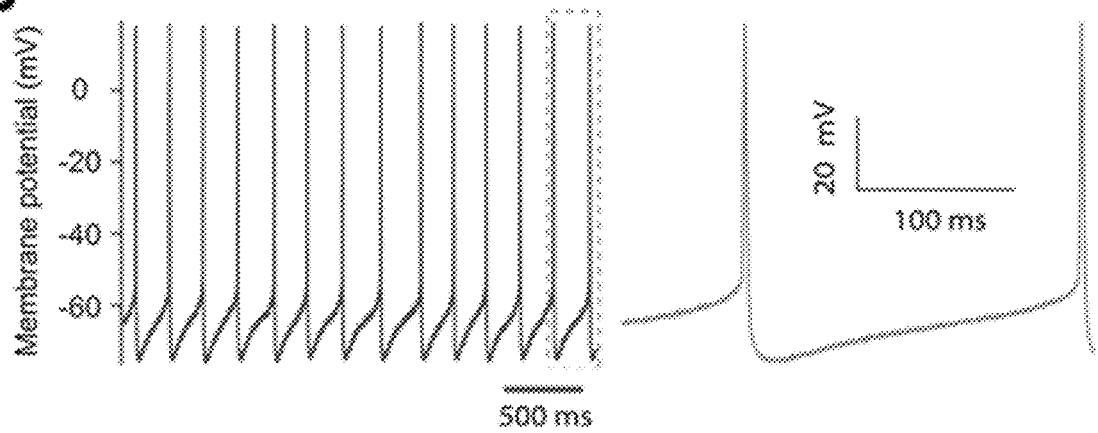
Figure 6C:
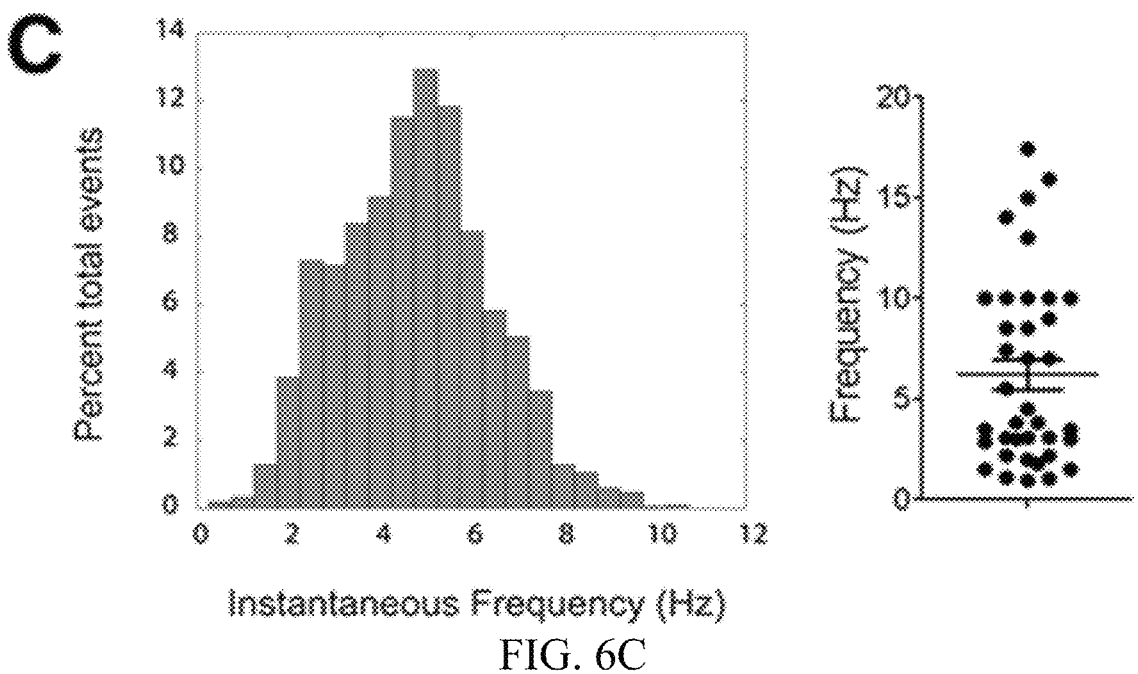

It has been well established that midbrain DA neurons are pacemaker neurons that discharge spontaneously at a rate between 1 and 10 Hz with an average rate of 4.5 Hz. To test whether Atoh1-induced DA neurons display similar electrophysiological properties to primary midbrain DA neurons, we performed patch-clamp recording in Atoh1-induced DA neurons (n=57) derived from human iPSCs at differentiation day 36-49 (FIG. 6A). In voltage-clamp experiments, the series input resistance of these Atoh1-induced DA neurons was 7.7±3 MΩ; the input resistance was 295.8±174.5 MΩ, and the average resting membrane potential was 75.3±9.9 mV. 64.9% of these neurons showed spontaneous spiking activity (FIG. 6B, n=37) with an amplitude of 66.1±18.3 mV and a mean frequency of 6.2±4.7 Hz (n=37; FIG. 6C). 26.3% of these neurons discharged action potentials during current injection either by depolarization or hyperpolarization (n=15), and only 8.7% (n=5) of these neurons did not have typical action potential either by positive or negative current injection.

Figure 6D:
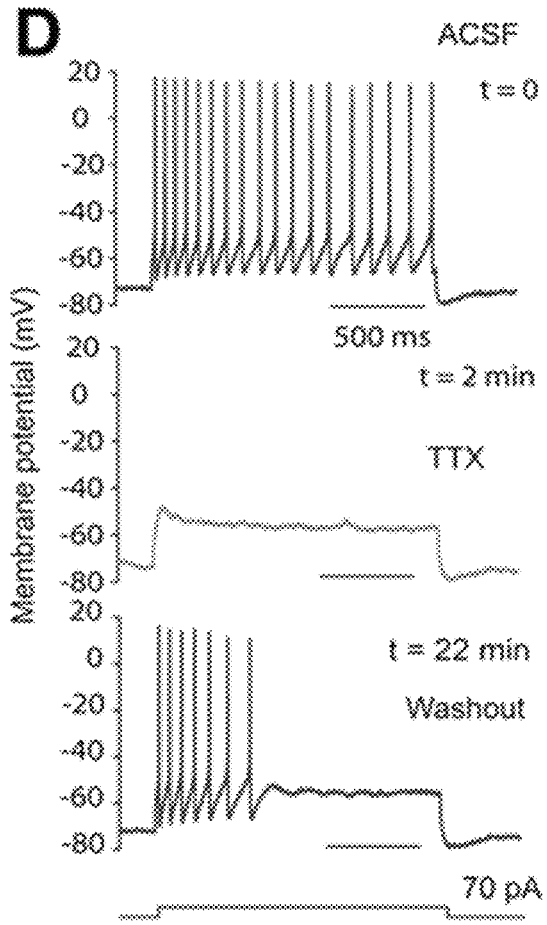

We further investigated the maturation of intrinsic ion channels in Atoh1-induced DA neurons. As shown in FIG. 6D, we first injected current (70 pA) to a neuron to depolarize the membrane potential. This induced a train of action potentials (FIG. 6D, up panel), which were completely blocked by the sodium channel blocker TTX (0.5 μM, 5 minutes administration, FIG. 6D, middle panel). This effect was reversed by TTX washout, after which the action potentials recovered in 17 minutes (FIG. 6D, bottom panel).

Midbrain DA neurons have been found to also have KCNQ potassium channels that contribute to their tonic spontaneous activity, and during hyperpolarization these neurons display a typical sag in voltage. Here, we injected negative current to hyperpolarize the membrane of Atoh1-induced neurons (FIG. 6E). This negative current injection produced hyperpolarization sag and rebound action potentials that resemble the tonic spontaneous spiking activity. Both events were blocked by ML252 (5 μM, a KCNQ2 inhibitor). We further investigated the voltage-sensitive sodium and potassium currents in voltage-clamp mode by elevating membrane potentials to different levels (FIG. 6F, left). After the treatment of sodium and potassium channel inhibitors (TTX (0.5 μM) and 4-AP (25 μM), respectively), both sodium and potassium currents are significantly attenuated (FIG. 6F, right).

Atoh1-Induced DA Neurons are Sensitive to 6-OHDA Treatment.

Figure 7A:
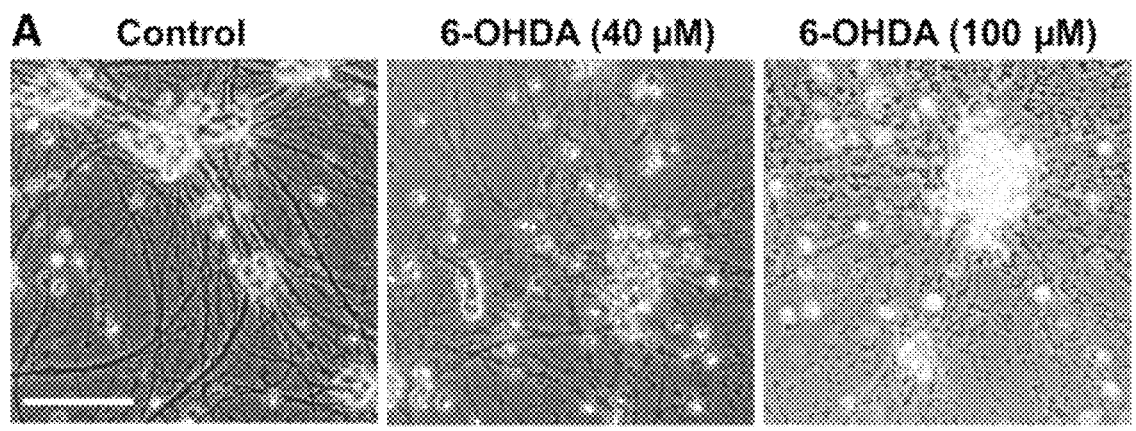
FIG. 7A-7B. Neurotoxicity induced by 6-OHDA in Atoh1-induced dopaminergic (DA) neurons. (A): Atoh1-induced DA neurons derived from Atoh1-iPSCs at differentiation day 36 were treated with 6-OHDA for 15 minutes. Bright-field microscope images show the morphological signs of neuron death at 24 hours after treatment. Scale bar=100 µm. (B): Cell death was quantified by LDH cytotoxicity assay. The data represent means±SEM (n=3). *, p<01 compared with control. Abbreviations: LDH, lactate dehydrogenase; 6-OHDA, 6-hydroxydopamine.
Figure 7B:
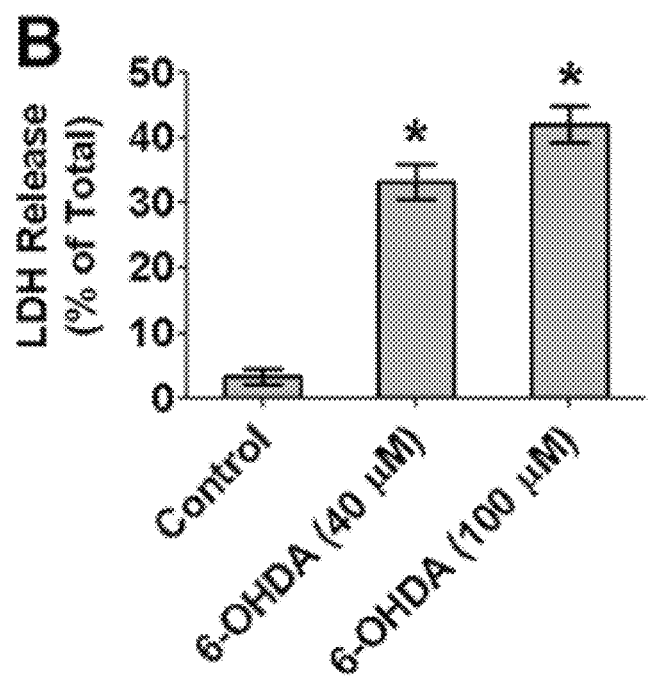

6-hydroxydopamine (6-OHDA) is a neurotoxin widely used to induce neurotoxicity both in vivo and in vitro to model DA neuron loss in PD pathogenesis. In neuron cultures from the substantia nigra of neonatal rat brains, 6-OHDA treatment at 40 μM causes selective DA neuron loss without affecting GABA neurons. Here, we tested the response of Atoh1-induced DA neurons to 6-OHDA treatment. 6-OHDA treatment (40 μM and 100 μM) for 15 minutes caused morphological signs of neuron death, including cell condensation and neurite fragmentation (FIG. 7A), and neuron death was also confirmed by LDH Cytotoxicity assay (FIG. 7B). Thus, Atoh1-induced DA neurons derived from human iPSCs are sensitive to 6-OHDA treatment at a concentration that selectively damages primary DA neurons isolated from substantia nigra.

Discussion

Human iPSCs provide a unique cell resource for establishing patient-specific disease models and for testing potential therapies. Due to the limited resource of human neurons, lineage-specific neurons derived from human iPSCs are the most desirable cells for modeling various neurological disorders, such as midbrain DA neurons for PD, striatal GABAergic neurons for Huntington's disease, and cholinergic motor neurons for amyotrophic lateral sclerosis. It is critical to develop highly efficient protocols for neuronal conversion in PSCs, in order to translate current iPSC-derived neuron models from small-scale laboratory applications to large-scale personalized drug testing platforms. Proneural transcription factors are core drivers of neurogenesis, and multiple members in this family (e.g., ASCL1, Ngn2 and NeuroD1) have been used to differentiate PSCs into neurons and more recently transdifferentiate somatic cells into neurons. We now show that Atoh1 is a highly efficient driver for neuronal conversion in PSCs, and Atoh1 induction in combination with cell extrinsic factors rapidly differentiates human PSC to functional DA neurons at high purity.

Multiple proneural transcription factors, e.g., ASCL1, Ngn2, and NeuroD1, are activated during the neuronal conversion of human PSCs, which initiate and sustain a neurogenic transcriptional network. We identified Atoh1 as a proneural transcription factor that is also upregulated during this neuronal conversion process. By using a Tet-On gene expression system to transiently induce ectopic Atoh1 expression in PSCs, we found that Atoh1 induction alone is sufficient for highly efficient neuronal conversion in PSCs. We further determined that 2 days are the minimal amount of time and that 4-5 days are ideal for transient Atoh1 induction in order to achieve successful neuronal conversion in PSCs. Several studies have suggested that Atoh1 and other proneural transcription factors are able to activate a neurogenic transcription factor network that over time becomes self-supporting. We also found that the neurogenic transcription factor NeuroD1 and Ngn2 were induced by ectopic Atoh1 and their expression was sustained after the silencing of exogenous Atoh1. This demonstrates that Atoh1-induced neuronal differentiation program in PSCs can become self-supporting and independent of exogenous Atoh1. It is noteworthy to mention that although exogenous Atoh1 was not detectable by western blotting after Dox withdrawal, Atoh1 expression did not return to baseline. This result is consistent with our previous result in FIG. 1B showing that endogenous Atoh1 is upregulated during the neuronal conversion of PSCs. The persistence of endogenous Atoh1 expression can be explained by the evidence that Atoh1 protein binds to its own enhancer to establish an autoregulation loop for maintaining its expression. Overall, our results support the mechanism that transient Atoh1 expression in PSCs can activate a cell-intrinsic program for neuronal commitment (a neuro-programming process). This process might share similar features to somatic cell reprogramming, where transient expression of reprogramming transcription factors induces the remodeling of epigenetic markers and drives cells into a self-sustaining pluripotent status. The epigenetic dynamics during this neuro-programming process warrants further studies, and a deep understanding of this process might lead to more potent approaches for converting both PSCs and somatic cells into neurons.

Proneural transcription factors have been shown to coordinately control the acquisition of a generic neuronal fate and the neuron subtype specification [9]. The functions of proneural transcription factors during neural development are strongly influenced by the spatial and temporal context including multiple modifiers such as transcriptional cofactors and cell extrinsic factors. Atoh1 has been found to drive the differentiation of numerous neuronal populations (e.g., cerebellar granule neurons, spinal cord neurons and inner ear hair cells), as well as diverse nonneuronal cell types (e.g., Merkel cells and intestinal secretory lineages), suggesting that the functions of Atoh1 depend on specific developmental contexts. When ectopic Atoh1 was expressed in the context of human PSCs, we detected a high percentage of neurons expressing the DA marker TH, and multiple DA neuron markers were induced in response to ectopic Atoh1 expression. Moreover, SHH and FGF8b, two neural patterning morphogens for DA specification, further promoted the expression of DA neuron markers and increased the efficiency of Atoh1-induced DA neuron conversion. These results suggest that Atoh1-induced neurons respond to extrinsic factors for generating lineage-specific neurons. A recent report shows that, in embryonic bodies derived from mouse ESCs, Atoh1 induction in combination with extrinsic factors promotes the generation of cerebellar granule neurons. Atoh1 induction has also been found to induce inner ear hair cell-like cells from mouse ESC-derived embryonic bodies. Overall, it is possible to derive different neuron subtypes from human or mouse PSCs by controlling the temporal induction of Atoh1 in various differentiation stages of PSCs and combining Atoh1 induction with different cell intrinsic and extrinsic factors (e.g., neuron-subtype-specific transcription factors or morphogens). Other proneural transcription factors also show this plasticity in specifying various neuron subtypes. For example, ASCL1 has been used to generate glutamatergic/GABAergic, DA and cholinergic neurons.

We established a highly efficient Atoh1-mediated approach for generating lineage-specific functional neurons from human PSCs. Inducible Atoh1 transgene was delivered using a single-vector Tet-On lentivirus and is stable in PSCs after >15 passages with puromycin selection (data not shown). Atoh1-induced DA neuron cultures derived from human iPSCs and ESCs showed >80% pan-neuronal purity and >80% DA subtype purity. This protocol yields DA neurons from PSCs with a rate of return of >250% or >100% after the cyropreservation of Atoh1-induced NPCs. The cryopreservation of Atoh1-induced DA NPCs will enable us to establish patient-specific DA neuron banks. After in vitro maturation, Atoh1-induced DA neurons expressed midbrain DA neuron markers (such as GIRK2, NURR1, FOXA2 and DAT) and exhibited robust synapse formation. The functional maturation of these DA neurons was further confirmed by DA release and spontaneous spiking activity. Overall, Atoh1-induced DA neurons derived from human iPSCs recapitulate key features of primary midbrain DA neurons, making this Atoh1-mediated approach particularly applicable for PD modeling using patient-derived iPSCs. It has been reported that primary DA neurons but not GABAergic neurons, from the substantia nigra of neonatal rat brains, are sensitive to 6-OHDA treatment at low concentration (40 µM). We also demonstrated that Atoh1-induced DA neurons showed similar 6-OHDA sensitivity to primary midbrain DA neurons, supporting that Atoh1-induced DA neurons can serve as a reliable neurotoxicity model for PD.

Due to the use of genome-integrating lentivirus for ectopic Atoh1 expression, our Atoh1-induced DA neurons will not be optimal for cell replacement therapy. However, we found that transient Atoh1 expression for 3-5 days is sufficient for highly efficient neuronal conversion in PSCs. Thus, non-integrating viruses (e.g., adenovirus and Sendai virus) should be suitable to overcome the limitation due to using lentivirus. More recently, multiple virus-free systems based on mRNA or protein delivery have been established to generate transgene-free human iPSCs [42-44], and these approaches can be applied to generate transplant-ready Atoh1-induced DA neurons. It is also noteworthy that chemical compounds that induce Atoh1 expression have been identified and patented (Patent Publication Number: US20090232780A1), thus providing another potential method for Atoh1 induction in PSCs that warrants further testing.

Conclusion

Atoh1 is a potent driver for highly efficient neuronal conversion in human PSCs. Atoh1 induction in combination with cell extrinsic factors differentiates PSCs into functional DA neurons in high purity. Atoh1-induced DA neurons derived from human iPSCs recapitulate key features of primary midbrain DA neurons and provide a useful cell model for studying the pathogenesis of both familial PD and, more importantly, sporadic PD, and testing potential PD therapies.

Figures 12A, 12B:
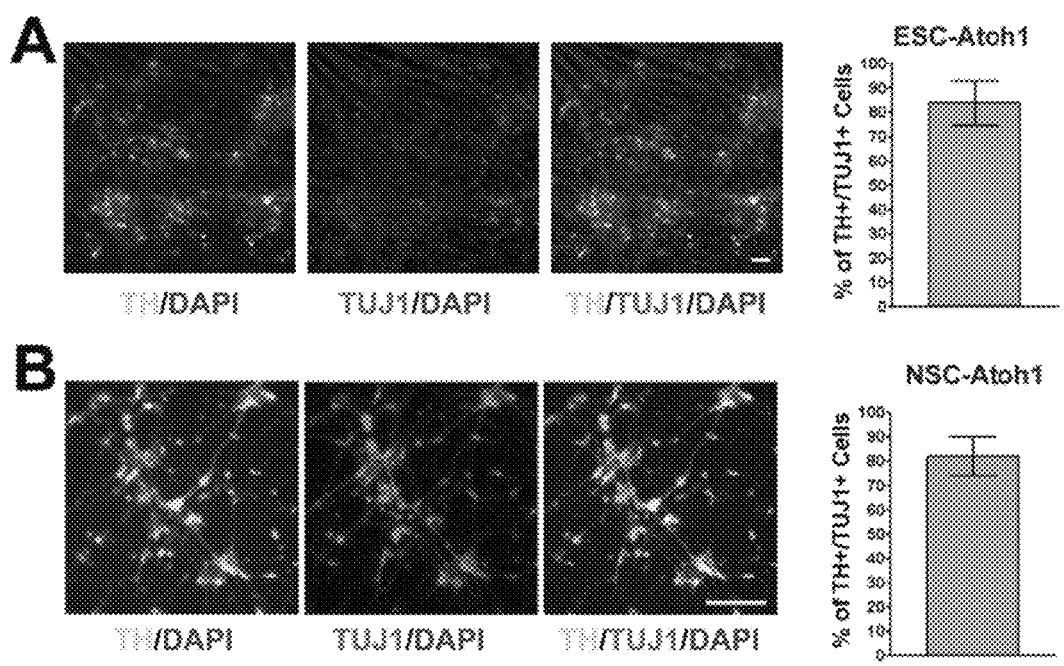
FIG. 12A-12B. Atoh1 induces highly efficient DA neuron differentiation in human ESCs and NSCs. (A) Atoh1-ESCs were differentiated following the protocol as shown in FIG. 4A and Table 2. Atoh1-induced neuron cultures at Day 36 were immunostained with antibody against neuronal lineage marker (TUJ1) and DA neuron marker (TH). Cell nuclei were counterstained with DAPI. (Bar: 20 µm). Cells from 10 random-selected microscopic fields were counted to calculate the percentage of TH+/TUJ1+ cells over DAPI+ cells (left panel, Data represents Mean±SEM). (B) Atoh1-NSCs were differentiated following the protocol as shown in FIG. 4A and Table 3. Atoh1-induced neuron cultures at Day 36 were immunostained with antibody against neuronal lineage marker (TUJ1) and DA neuron marker (TH). Cell nuclei were counterstained with DAPI. (Bar: 20 µm). Cells from 10 random-selected microscopic fields were counted to calculate the percentage of TH+/TUJ1+ cells over DAPI+ cells (left panel, Data represents Mean±SEM).

Example 2: Atoh1-Mediated Differentiation of Human ESCs and NSCs into DA Neurons Atoh1-ESCs were differentiated following the protocol as shown in FIG. 4A and Table 2. Atoh1-induced neuron cultures at Day 36 co-expressed neuronal and DA neuron markers, β-tubulin III (TUJ1) and tyrosine hydroxylase (TH), respectively (FIG. 12A). The Atoh1 induction protocol yielded DA neurons from human ESCs with 84±9% purity as determined by the percentage of TUJ+/TH+ cells (FIG. 12A). Atoh1-NSCs were differentiated following the protocol as shown in FIG. 4A and Table 3. Atoh1-induced neuron cultures at Day 36 co-expressed neuronal marker (β-tubulin III, TUJ1) and DA neuron marker (tyrosine hydroxylase, TH) (FIG. 12B). The Atoh1 induction protocol yielded DA neurons from human NSCs with 82±8% purity as determined by the percentage of TUJ+/TH+ cells (FIG. 12B).

TABLE 2

DA neuron differentiation media used in Atoh1-induced protocol as shown in FIG. 4A

| Day | Medium | Additives |
|---|---|---|
| 0 | E8 | Y-27632 |
| 1 | E6 (75%) + N2 (25%) | Doxycyline/SHH/FGF-8b |
| 2 | E6 (50%) + N2 (50%) | Doxycyline/SHH/FGF-8b |
| 3 | E6 (25%) + N2 (75%) | Doxycyline/SHH/FGF-8b |
| 4 | N2 | Doxycyline/SHH/FGF-8b |
| 5 | N2 | Doxycyline/SHH/FGF-8b |
| 6 | N2 (50%) + B27 (50%) | |
| 7 | B27 | |
| 8-36 | B27 | B/G/T/C/A/D |

E8: Essential 8 Medium
E6: Essential 6 Medium
N2: DMEM/F12 medium with N2 supplement (1:100)
B27: neurobasal medium with B27 supplement (1:50)
Doxycyline (0.5 μg/ml);
Y-27632 (10 μM)
SHH: Sonic Hedgehog (200 ng/ml);
FGF-8b (100 ng/ml)
B/G/T/C/A/D: BDNF (20 ng/ml)/GDNF (10 ng/ml)/TGF-β3 (1 ng/ml)/Dibutyryl cAMP (0.5 mM)/Ascorbic Acid (0.2 mM)/DAPT (10 μM)

TABLE 3

DA neuron differentiation media used in Atoh1-induced protocol as shown in FIG. 4A
NSC Differentiation

| Day | Medium | Additives |
|---|---|---|
| 0 | N2 | bFGF |
| 1 | N2 | Doxycyline/SHH/FGF-8b |
| 2 | N2 | Doxycyline/SHH/FGF-8b |
| 3 | N2 | Doxycyline/SHH/FGF-8b |
| 4 | N2 | Doxycyline/SHH/FGF-8b |
| 5 | N2 | Doxycyline/SHH/FGF-8b |
| 6 | N2 (50%) + B27 (50%) | |
| 7 | B27 | |
| 8-36 | B27 | B/G/T/C/A/D |

E8: Essential 8 Medium
E6: Essential 6 Medium
N2: DMEM/F12 medium with N2 supplement (1:100)
B27: neurobasal medium with B27 supplement (1:50)
bFGF (10 ng/ml);
SHH: Sonic Hedgehog (200 ng/ml);
FGF-8b (100 ng/ml)
B/G/T/C/A/D: BDNF (20 ng/ml)/GDNF (10 ng/ml)/TGF-β3 (1 ng/ml)/Dibutyryl cAMP (0.5 mM)/Ascorbic Acid (0.2 mM)/DAPT (10 μM)

Example 3: Atoh1-Mediated Differentiation of Human iPSCs into Dopaminergic (DA) Neurons As shown in FIG. 4A, we established protocols for differentiating human iPSCs into DA neurons by Atoh1 and other additives (sonic hedgehog and FGF-8b). The recipes for cell culture media are listed in Table 2. Cells were plated ($4 \times 10^4$ cells per cm$^2$) on matrigel (BD) in Essential 8 Medium (Life Technologies) with ROCK inhibitor (Y-27632, Stemgent). From Day 1 to Day 7, cell culture medium was changed every day. From Day 8 to Day 36, half of the cell culture medium was changed every 3-4 days. At day 36 of differentiation, these neurons co-expressed neuronal marker (β-tubulin III, TUJ1) and DA neuron marker (tyrosine hydroxylase, TH), the rate-limiting enzyme in the synthesis of dopamine (FIG. 4C). The Atoh1 induction protocol yielded DA neurons with 89±6% purity as determined by the percentage of TUJ+/TH+ cells (FIG. 4D). Moreover, the Atoh1-induced DA neurons also co-expressed other midbrain DA neuron markers, such as G-protein-regulated inward-rectifier potassium channel 2 (GIRK2), forkhead box protein A2 (FOXA2) and dopamine transporter (DAT) (FIGS. 6A, 6B and 6C), which are also expressed in substantia nigra pars compacta (SNPC) DA neurons. By day 60, these DA neurons show extensive TUJI+ nerve fiber growth and robustly express mature neuron marker (synapsin) (FIG. 6C).

Figures 13A, 13B, 13C, 13D:
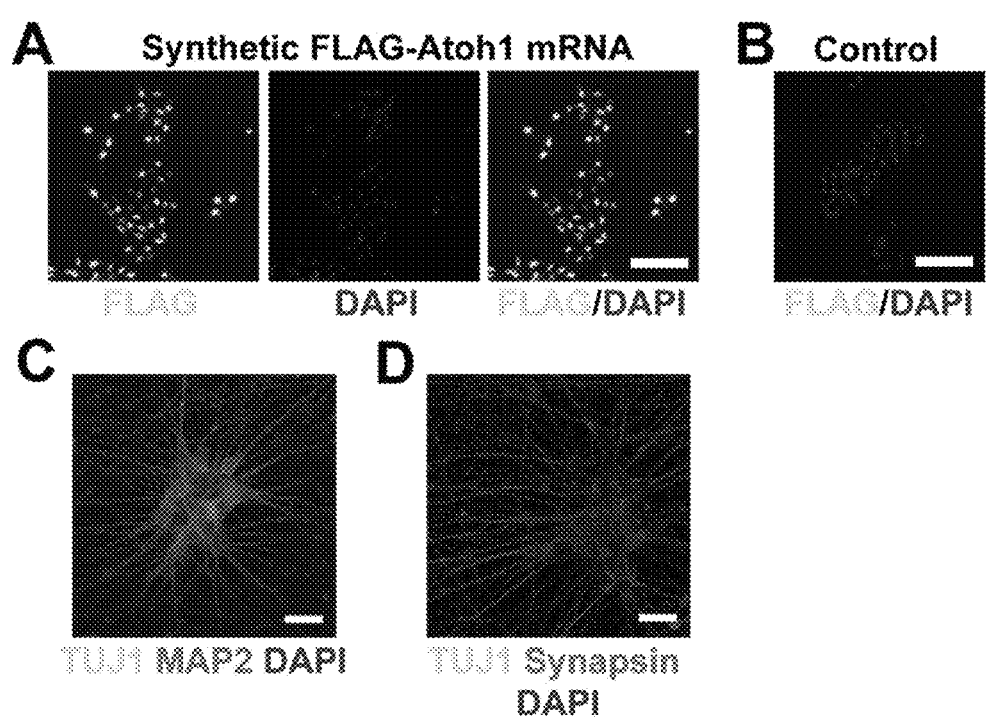
FIG. 13A-13D. Synthetic mRNA encoding Atoh1 drives the differentiation of human iPSCs into neurons. Ectopic Atoh1 (with N-terminal FLAG tag) expression was detected in >90% of the Atoh1-mRNA-transfected cells (FIG. 13A) but not in untransfected control cells (FIG. 13B), as determined by FLAG immunofluorencence staining. After iPSCs received daily transfection of Atoh1 mRNA for 4 days, cells were replated (3×10$^5$ cells per cm$^2$) on dishes pre-coated with poly-D-Lysine (1 µg/ml) and laminin (1 µg/ml). Neurons after being matured in vitro for 20 days co-express the neuronal marker (TUJ1) and the mature neuron markers (MAP2 and Synapsin) (FIGS. 13C and 13D). Overall, these results demonstrate that Atoh1 can be induced in human SCs by delivering synthetic Atoh1 mRNA, and Atoh1 mRNA delivery drives neuronal conversion of human SCs.

Example 4: Synthetic mRNA Encoding Atoh1 Drives the Differentiation of Human iPSCs into Neurons We further tested Atoh1 induction in iPSCs by using synthetic mRNAs encoding Atoh1. A cDNA encoding Atoh1 protein with an N-terminal FLAG tag was cloned into a DNA vector with T7 promoter for in vitro mRNA synthesis. The synthesis of Atoh1 mRNA was performed by using the mMESSAGE mMACHINE® T7 ULTRA Transcription Kit (Ambion). Synthetic Atoh1 mRNA was transfected into human iPSCs cultured in the 24-well plate (0.25 μg mRNA per well) using a lipid-based mRNA transfection reagent. Ectopic Atoh1 expression was detected in >90% of the Atoh1-mRNA-transfected cells (FIG. 13A) but not in untransfected control cells (FIG. 13B), as determined by FLAG immunofluorencence staining. After iPSCs received daily transfection of Atoh1 mRNA for 4 days, cells were replated ($3 \times 10^5$ cells per cm$^2$) on dishes pre-coated with poly-D-Lysine (1 μg/ml) and laminin (1 μg/ml). Neurons after being matured in vitro for 20 days co-express the neuronal marker (TUJ1) and the mature neuron markers (MAP2 and Synapsin) (FIGS. 13C and 13D). Overall, these results demonstrate that Atoh1 can be induced in human SCs by delivering synthetic Atoh1 mRNA, and Atoh1 mRNA delivery drives neuronal conversion of human SCs.

Figure 14A:
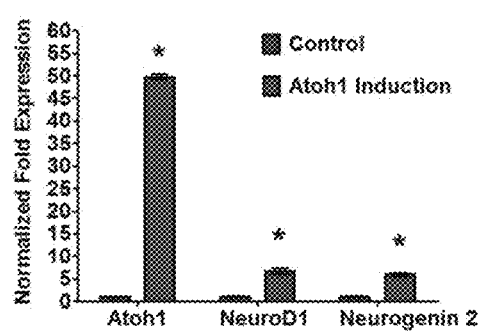
FIG. 14A-14C. Neurogenin 2 can be induced by Atoh1 and also drives the differentiation of human iPSCs into neurons. (A) Atoh1 induction in human iPSCs for 2 days activated known Atoh1 target NeuroD1 and the proneural transcription factor Neurogenin 2 that has not yet been defined as an Atoh1 target gene (FIG. 14A), as determined by quantifying gene expression using quantitative real-time PCR. (B) We further tested if the Atoh1 target gene Neurogenin 2 can also drive lineage-specific neuronal conversion of human iPSCs. We applied the same lentivirus-mediated gene delivery system as that for Atoh1 expression (FIG. 2A) to achieve Dox inducible expression of Neurogenin 2 in human SCs. By following the differentiation strategy as shown in FIG. 14B, we successfully generated TH+/TUJ1+ DA neurons from human iPSCs by inducing Neurogenin 2 in combination with two morphogens (sonic hedgehog (SHH) and FGF-8b) (FIG. 14C). These results demonstrate that Atoh1-induced gene targets (e.g. Neurogenin 2) can be used to drive lineage-specific neuronal conversion of human SCs.
Figure 14B:
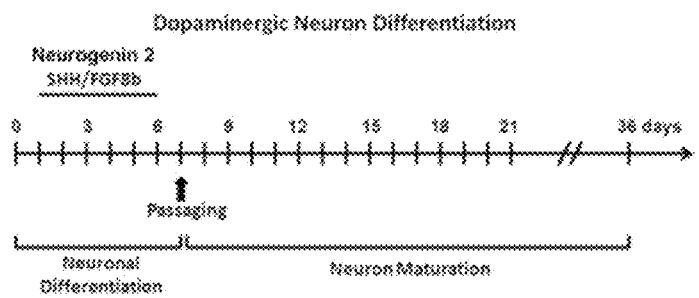
Figure 14C:
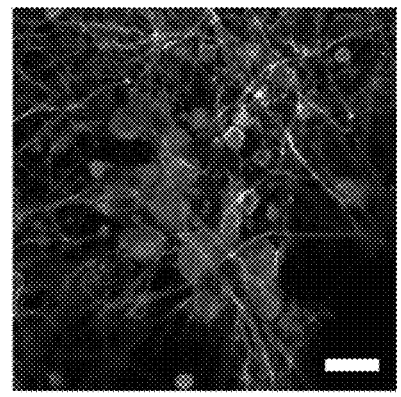

Example 5: Neurogenin 2 can be Induced by Atoh1 and Also Drives the Differentiation of Human iPSCs into Neurons Atoh1 can activate crucial neurogenic transcription factors, such as NeuroD1, 2, 6 and Nhlh1, 2, to initiate a neuronal differentiation program that later becomes self-supporting and Atoh1-independent. Here, we found that Atoh1 induction in human iPSCs for 2 days activated known Atoh1 target NeuroD1 and the proneural transcription factor Neurogenin 2 that has not yet been defined as an Atoh1 target gene (FIG. 14A), as determined by quantifying gene expression using quantitative real-time PCR. We further tested if the Atoh1 target gene Neurogenin 2 can also drive lineage-specific neuronal conversion of human iPSCs. We applied the same lentivirus-mediated gene delivery system as that for Atoh1 expression (FIG. 2A) to achieve Dox inducible expression of Neurogenin 2 in human SCs. By following the differentiation strategy as shown in FIG. 14B, we successfully generated TH+/TUJ1+DA neurons from human iPSCs by inducing Neurogenin 2 in combination with two morphogens (sonic hedgehog (SHH) and FGF-8b) (FIG. 14C). These results demonstrate that Atoh1-induced gene targets (e.g. Neurogenin 2) can be used to drive lineage-specific neuronal conversion of human SCs.

We claim:

1. A method of inducing differentiation of human stem cells into dopaminergic (DA) neurons comprising the steps of:
   a. transfecting human stem cells with an Atoh1 messenger ribonucleic acid (mRNA); and
   b. growing the transfected cells in culture in the presence of Dox, Sonic Hedgehog (SHH) and FGF-8b until DA neurons are induced.

2. The method of claim 1, wherein the human stem cells are induced pluripotent stem cells (iPSCs).

3. The method of claim 1, wherein the human stem cells are embryonic stem cells (ESCs).

4. The method of claim 2, wherein the human stem cells are neural stem cells (NSCs).

5. The method of claim 1, wherein prior to step (b), the method further comprises the step of transfecting the human stem cells a NeuroD1 mRNA.

6. The method of claim 5, wherein prior to step (b), the method further comprises the step of transfecting the human stem cells with a Neurogenin 2 mRNA.

* * * * *